United States Patent [19]

Adams et al.

[11] Patent Number: 5,242,809

[45] Date of Patent: Sep. 7, 1993

[54] GAL OPERON OF STREPTOMYCES

[75] Inventors: Craig W. Adams, Corona, Calif.; Mary E. Brawner, Wayne; James A. Fornwald, Norristown, both of Pa.; Francis J. Schmidt, Columbia, Mo.

[73] Assignee: SmithKline Beecham Corporation, Philadelphia, Pa.

[21] Appl. No.: 967,949

[22] Filed: Oct. 27, 1992

Related U.S. Application Data

[63] Continuation of Ser. No. 692,769, Apr. 29, 1991, abandoned, which is a continuation-in-part of Ser. No. 9,419, Jan. 30, 1987, abandoned, which is a continuation-in-part of Ser. No. 834,706, Feb. 28, 1986, abandoned.

[51] Int. Cl.$^5$ .................... C12N 15/09; C12N 15/74; C12N 15/11

[52] U.S. Cl. .................... 435/69.1; 435/172.3; 435/320.1; 435/252.3; 435/252.35; 536/24.1; 935/41; 935/75

[58] Field of Search .............. 435/69.1, 172.3, 320.1, 435/252.35, 252.3; 536/24.1; 935/41, 75

[56] References Cited

PUBLICATIONS

Thompson et al. 1982 Gene 20: 51–62.
Casaban J. Mol. Biol. 1976 104(2) 557–566.

Primary Examiner—Richard A. Schwartz
Assistant Examiner—John Guyader
Attorney, Agent, or Firm—Carol G. Canter; Edward T. Lentz; Stuart R. Suter

[57] ABSTRACT

A recombinant DNA molecule comprising the *Streptomyces gal* operon galK gene; galE gene; galT gene; P1 promoter, P2 promoter, P2 promoter expression unit; P1 promoter regulated region; or the entire *Streptomyces gal* operon.

43 Claims, 3 Drawing Sheets

GAL OPERON OF STREPTOMYCES

This is a continuation of application Ser. No. 07/692,769 filed Apr. 29, 1991, now abandoned, which is a continuation-in-part of Ser. No. 07/009,419 filed Jan. 30, 1987, now abandoned, which is continuation-in-part of Ser. No. 06/834,706 filed Feb. 28, 1986, now abandoned.

BACKGROUND OF THE INVENTION

This invention relates to a recombinant DNA molecule comprising the Streptomyces gal operon.

Hodgson, J. Gen. Micro., 128, 2417-2430 (1982), report that Streptomyces coelicolor A3(2) has a glucose repression system which allows repression at the level of transcription of the arabinose uptake system, one of the glycerol uptake systems, and also repression of the galactose uptake system in wild type strains. There is no report in Hodgson of actual galactose metabolism by S. coelicolor A3(2).

Okeda et a. Mol. Gen. Genet., 196, 501-507 (1984), report that glucose kinase activity, 2-deoxyglu-cose-sensitivity, glucose utilization and glucose repression were all restored to S. coelicolor A3(2) glk (glucose kinase) mutants transformed by a 3.5 kb DNA fragment which contained the glk gene cloned from S. coelicolor into a phage vector.

Seno et al., Mol. Gen. Genet., 193, 119-128 (1984), report the glycerol (gyl) operon of Streptomyces coelicolor, and state such operon is substrate-inducible and catabolite-repressible.

Debouck, et al., Nuc. Acids, Res., 13(6), 1841-1853 (1985), report that the gal operon of E. coli consists of three structurally contiguous genes which specify the enzymes required for the metabolism of galactose, i.e., galE (uridine diphosphogalactose-4-epimerase), galT (galactose-1-phosphate uridyltransferase) and galK (galactokinase) that such genes are expressed from a polycistronic mRNA in the order E, T, K; that the expression of the promoter distal gene of the operon, galK, is known to be coupled translationally to the galT gene immediately preceding it; that such translational coupling results from a structural overlap between the end of the galT coding sequence and the ribosome binding region of galK; and that the translational coupling of galT and galK ensures the coordinate expression of these genes during the metabolism of galactose.

SUMMARY OF THE INVENTION

This invention relates to a recombinant DNA molecule comprising a Streptomyces gal operon galK gene; galE gene; galT gene; P2 promoter expression unit, or P2 promoter or any functional derivative thereof as well as a recombinant DNA molecule comprising a Streptomyces gal operon P1 promoter, P1 promoter regulated region or the entire gal operon or any regulatable and functional derivative thereof.

This invention also relates to a recombinant DNA molecule comprising the Streptomyces gal operon or any regulatable and functional derivative thereof; a recombinant DNA molecule comprising a Streptomyces lividans or Streptomyces coelicolor gal operon containing a wild-type gal operon P1 promoter or any regulatable and functional P1 promoter derivative, a functional DNA molecule operatively linked to such operon; a recombinant DNA vector comprising and such DNA molecule, and, optionally, additionally comprising a replicon; a method of preparing a host cell transformed with such vector; the transformed host prepared by such method; a method of expressing such functional DNA sequence which comprises cultivating such transformed host under suitable conditions such that the functional DNA sequence is expressed; and to a method of regulating the expression of such functional DNA sequence which comprises cultivating such transformed host under conditions which regulate such expression.

This invention also relates to a recombinant DNA molecule comprising the Streptomyces gal operon P2 promoter expression unit or any functional derivative thereof and a functional DNA molecule operatively linked to such unit; a recombinant DNA vector comprising such DNA molecule, and, optionally, additionally comprising a replicon; a method of preparing a host cell transformed with such vector; the transformed host prepared by such method; and to a method of expressing such functional DNA sequence which comprises cultivating such transformed host under suitable conditions such that the functional DNA sequence is expressed.

This invention also relates to a recombinant DNA molecule comprising the Streptomyces gal operon P1 promoter regulated region or any regulatable and functional derivative thereof and a functional DNA molecule operatively linked to such region; a recombinant DNA vector comprising such DNA molecule, and, optionally,, additionally comprising a replicon; a method of preparing a host cell transformed with such vector, the transformed host prepared by such method; a method of expressing such functional DNA sequence which comprises cultivating such transformed host under suitable conditions such that the functional DNA sequence is expressed; and to a method of regulating the expression of such functional DNA sequence which comprises cultivating such transformed host under conditions which regulate such expression.

This invention also relates to a recombinant DNA molecule comprising the Streptomyces gal operon P1 promoter or any regulator and functional derivative thereof and a foreign functional DNA molecule operatively linked to such region; a recombinant DNA vector comprising such DNA molecule, and, optionally, additionally comprising a replicon; a method of preparing a host cell transformed with such vector; the transformed host prepared by such method; a method of expressing such functional DNA sequence which comprises cultivating such transformed host under suitable conditions such that the functional DNA sequence is expressed; and to a method of regulating the expression of such functional DNA sequence which comprises cultivating such transformed host under conditions which regulate such expression.

This invention also relates to a recombinant DNA molecule comprising the Streptomyces gal operon P2 promoter or any functional derivative thereof and a foreign functional DNA molecule operatively linked to such region; a recombinant DNA vector comprising such DNA molecule, and, optionally, additionally comprising a replicon; a method of preparing a host cell transformed with such vector; the transformed host prepared by such method; and to a method of expressing such functional DNA sequence which comprises cultivating such transformed host under suitable conditions such that the functional DNA sequence is expressed.

This invention also relates to a method of enabling a non-galactose utilizing host microorganism or cell to utilize galactose which comprises transforming such host with a recombinant DNA molecule comprising a *Streptomyces gal* operon or any portion of the *Streptomyces gal* operon, or any functional derivative thereof, which is adequate to enable such transformed host to utilize galactose. This invention relates to the recombinant DNA vector employed in such method and to the host prepared by such method.

DETAILED DESCRIPTION OF THE INVENTION

Figure 1:
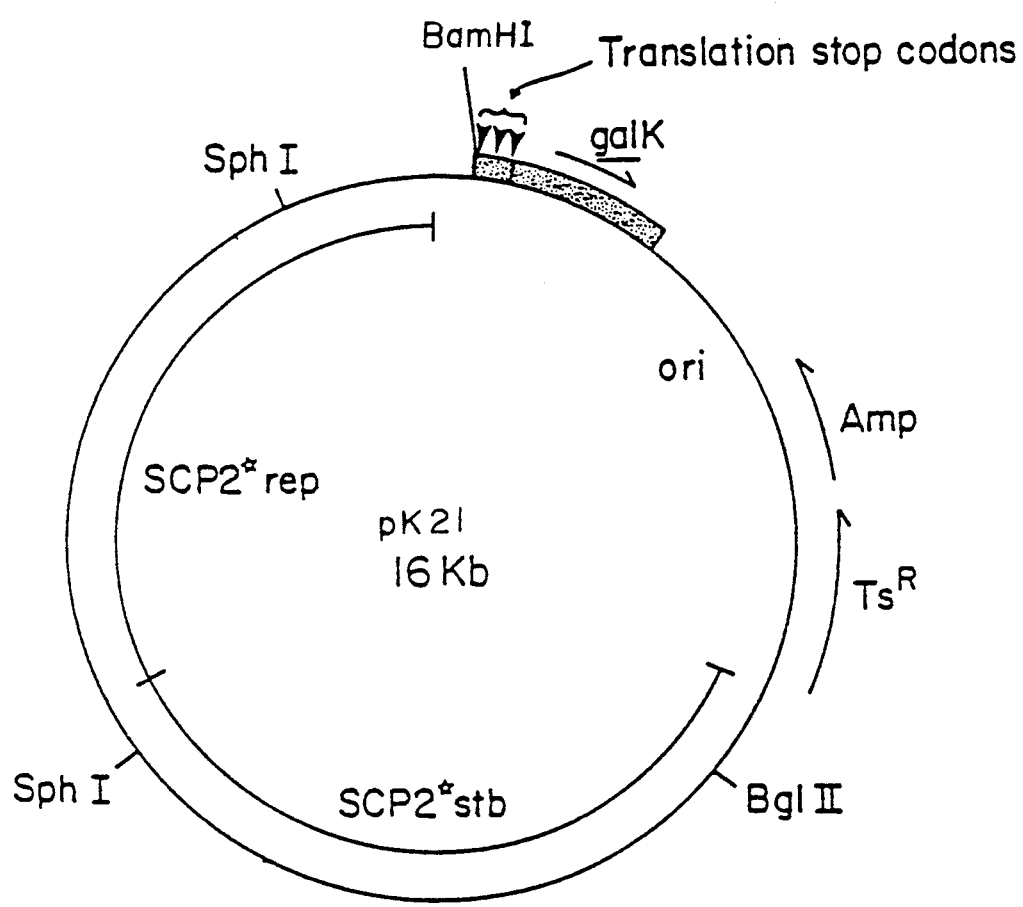
FIG. 1 represents a restriction endonuclease map of the *Streptomyces lividans* 1326 galactose (gal) operon and indicates approximate locations for structural genes and promoters within the operon.

It has now been discovered that the Streptomyces genome contains an operon for the metabolism of galactose (i.e., a gal operon) which comprises three structural genes (galT, galE and galK) and two promoters (P1 and P2). The galT gene product is known as galactose-1-phosphate uridyltransferase (transferase), the galE gene product is known as uridine diphosphogalactose-4-epimerase (epimerase), and the galK gene product is known as galactose-1-kinase (galactokinase). The function of the gene products of galT, galE and galK in galactose metabolism in Streptomyces is explained by the following diagram:

---

1. galactose + ATP  galactokinase
   galactose-1-phosphate + ADP
2. galactose-1-phosphate + UDP-glucose  transferase
   UDP-galactose + glucose-1-phosphate
3. UDP-galactose  epimerase  UDP-glucose

---

By the term "promoter" is meant any region upstream of a structural gene which permits binding of RNA polymerase and transcription to occur.

By the term "structural gene" is meant a coding sequence for a polypeptide which serves to be the template for the synthesis of mRNA.

By the term "operon" is meant a group of closely linked genes responsible for the synthesis of one or a group of enzymes which are functionally related as members of one enzyme system. An operon comprises an operator gene, a number of structural genes (equivalent to the number of enzymes in the system) and a regulator gene. By "operator" or "operator gene" is meant a DNA sequence which controls the biosynthesis of the contiguous structural gene(s) within an operon. By "regulator gene" is meant a gene which controls the operator gene in an operon through the production of a repressor which can be either active (enzyme induction) or inactive (enzyme repression). The transcription of the structural gene(s) in an operon is switched on or off by the operator gene which is itself controlled in one or more of three ways: 1) in inducible enzyme systems, the operator is switched off by a repressor produced by the regulator gene and which can be inactivated by some metabolite or signal substance (an inducer) coming from elsewhere in the cell or outside the cell, so that the presence of the inducer results in the operon becoming active; or 2) in repressed enzyme systems, the operator is switched off by a repressor-corepressor complex which is a combination of an inactive repressor produced by the regulator gene with a corepressor from elsewhere, so that the presence of the corepressor renders the operon inactive; or 3) in activated gene systems, the promoter is switched on by an activator produced by a regulator gene which can be activated by some metabolic or signal substance.

The *Streptomyces gal* operon is naturally present in the Streptomyces genome.

By the term "*Streptomyces gal* operon" is meant that region of the Streptomyces genome which comprises the P1 promoter, P2 promoter, galT, galE and galK structural genes and any other regulatory regions required for transcription and translation of such structural genes.

By the term "regulatory region" is meant a DNA sequence, such as a promoter or operator, which regulates transcription of a structural gene.

The following model is suggested for gene expression within the *Streptomyces gal* operon. The P1 promoter is a galactose inducible promoter (i.e., it is induced in the presence of galactose and repressed in the presence of glucose). According to S1 data, the P2 promoter is constitutive, i.e., it is "turned on" regardless of the presence or absence of galactose or any other carbon source.

A cosmid library was constructed for *Streptomyces lividans* 1326 DNA by using cosmid pJW357 (which encodes the ability to replicate in both Streptomyces and *E. coli*.

This library was then transfected into *E. coli* K21 which is a derivative of the *E. coli* strain MM294 which contained a bacteriophage P1 transduced galactokinase (galK) mutation. Transfected cells were plated under media conditions which select for both the presence of the cosmid and the presence of an active galK gene. Weakly positive colonies were isolated and the cosmid DNA derived from these colonies was transformed into the K21 strain. These transformations yielded two cosmids which consistently produced positive growth with galactose as the only carbon source. These galK+ cosmids were then transformed into a Streptomyces host (i.e., *Streptomyces lividans* 1326-12K) which had been isolated by the inventors of the subject invention as unable to grow on medium in which galactose was the only carbon source by using 2-deoxygalactose selection [see, Brawner et al., *Gene*, 40, 191 (1985), in press]. Under conditions which differentiate strains able and unable to produce galactokinase, only one of the cosmids caused the *Streptomyces lividans* 1326-12K host to become galK+. Further studies have demonstrated that this cosmid encodes a gene with galactokinase activity. Additional studies, including DNA sequence analysis and protein studies demonstrate that the Streptomyces gene shares homology with the *E. coli* and yeast galactokinase genes. Regulation studies indicate that the cosmid encoded galactokinase gene regulated in the same manner as the chromosome encoded gene.

A *S. lividans* gal operon was originally isolated from a ca. 9 kilobase (Kb) region of *Streptomyces lividans* 1326. The ca. 9 Kb region of *Streptomyces lividans* 1326 containing the Streptomyces gal operon has been mapped substantially as follows in Table A. By "substantially" is meant (i) that the relative positions of the restriction sites are approximate, (ii) that one or more restriction sites can be lost or gained by mutations not otherwise significantly affecting the operon, and (iii) that additional sites for the indicated enzymes and, especially for enzymes not tested, may exist. The restriction enzymes used herein are commercially available. All are described by Roberts, *Nuc. Acids. Res.*, 10(5);p117 (1982).

TABLE A

| Map Position | Restriction Enzyme | Location (kb) |
|---|---|---|
| 1 | HindIII | −.40 |
| 1a | NruI | 0 |
| 2 | BglII | .75 |
| 3 | EcoRI | 1.05 |
| 4 | PvuII | 1.15 |
| 5 | MluI | 2.30 |
| 6 | PvuII | 2.80 |
| 7 | EcoRI | 4.00 |
| 8 | PvuII | 4.10 |
| 8a | SacI | 4.25 |
| 9 | PvuII | 5.00 |
| 10 | XhoI | 5.50 |
| 11 | BamHI | 5.80 |
| 12 | BamHI | 6.50 |
| 13 | MluI | 6.90 |
| 13a | PvuII | 7.20 |
| 14 | MluI | 7.80 |
| 15 | BamHI | 8.00 |
| 16 | SphI | 8.30 |

FIG. 1 represents a restriction endonuclease map of the *Streptomyces lividans* 1326 gal operon and indicates locations for structural genes (galT, galE and galK) and promoters (P1 and P2) comprised within the operon.

Referring to Table A and FIG. 1, the location of the promoters and structural genes of the *Streptomyces lividans* 1326 gal operon are mapped substantially as follows in Table B:

TABLE B

| | Location (Kb) |
|---|---|
| P1 transcription start site | .10 |
| galT translation initiation codon | .15 |
| P2 transcription start site | 1.25 |
| galE translation initiation codon | 1.50 |
| galK translation initiation codon | 2.40 |
| 3' end of galK message | 3.60 |

Microorganisms of the genus have historically been used as a source of antibiotics for the pharmaceutical industry. Consequently, the technical skills necessary to scale-up the production of biological products using Streptomyces as the vehicle for the production of such products are presently available. However, before Streptomyces can be used as a vehicle for the production of bioactive molecules using the new recombinant DNA technologies, there is a need to define regulatory elements in Streptomyces analogous to those which have proved useful in *E. coli*. These regulatory elements include ribosomal binding sites and regulated transcriptional elements.

The existence of a galE, galT or galK gene or gene product or gal operon in Streptomyces has not been previously reported. The instant invention, i.e., the cloning of the *Streptomyces gal* operon, enables construction of regulatable expression/cloning vectors in Streptomyces, other actinomycetes, and other host organisms. Furthermore, the instant invention led to the discovery that the *Streptomyces gal* operon is polycistronic. Perhaps the most important feature of the cloning of the *Streptomyces gal* operon is the observation that there are sequences essential for regulation of the *Streptomyces galK* gene. Direct analogy to the initial use of the lac promoter from *E. coli* as an expression system can be made. In fact, Brosius et al., *Proc. Natl. Acad. Sci. USA*, 81 6929–6933 (1984), utilized the regulatory elements of the *E. coli* lac promoter to regulate the exceptionally strong *E. coli* ribosomal promoters. Because it is likely that the *Streptomyces gal* operon ribosomal promoters are also exceptionally strong, such promoters enable the construction of regulatable expression vectors which will be very useful in Streptomyces, other actinomycetes, and other host organisms. The instant invention also enabled the unexpected discovery that the 2-deoxygalactose selection which has been used in *E. coli* to select for galK mutants also operates in Streptomyces to select for galK mutants [see, Brawner et al., *Gene* 40, 191 (1985), in press]. This observation, combined with the ability to clone the *Streptomyces galK* gene and the promoter and regulatory regions required for its transcription and translation on a cosmid, as described herein, allows the direct insertion of any structural gene into the chromosomally located galK gene of Streptomyces by homologous recombination. This manipulation will allow molecular biologists to stably insert DNA fragments of interest into the Streptomyces chromosome. Such an approach will allow researchers to tag or mark a Streptomyces strain of interest or to insert expression cassettes into the organism without the need of maintaining an antibiotic selection such as that presently required by most Streptomyces expression vectors.

This invention relates to a recombinant DNA molecule comprising the *Streptomyces gal* operon on any regulatable and functional derivative thereof. By "regulatable and functional derivative" is meant any derivative of the *Streptomyces gal* operon which functions in substantially the same way as the naturally occurring *Streptomyces gal* operon in terms of regulatable production of the galT, galE and galK gene products. Such derivatives include partial sequences of the gal operon, as well as derivatives produced by modification of the gal operon coding sequence. Techniques for modifying the gal operon which are known in the art include, for example, treatment with chemical mutagens, irradiation or direct genetic engineering, such as by inserting, deleting or substituting nucleic acids by the use of enzymes or recombination techniques. The naturally occurring *Streptomyces gal* operon can be isolated from any galactose utilizing Streptomyces strain by employing the techniques described herein.

Numerous strains of various Streptomyces species are publicly available from many sources. For example, the American Type Culture Collection, Rockville, Md., U.S.A. has approximately 400 different species of Streptomyces available to the public. The ability of a particular strain of Streptomyces to utilize galactose can be readily determined by conventional techniques, such as by growing such strain on a medium containing galactose as the sole carbon source. The preferred Streptomyces species from which to isolate a gal operon include *S. lividans, S. coelicolor, S. azuraeus* and *S. albus, S. carzinostaticus, S. antibibrinolyticus* and *S. longisporus, S. lividans* is most preferred. The *Streptomyces gal* operon, and smaller portions thereof, is useful as a nucleic acid probe to obtain homologous sequences from other cells and organisms. The *Streptomyces gal* operon is also useful as a selection marker in an appropriate host mutant, and for providing regulatory elements. By "appropriate host mutant" is meant a host which does not utilize galactose because it (a) does not contain a gal operon or (b) contains a nonfunctional gal operon, or (c) contains a defect within a homologous structural gene or regulatory region comprised by the *Streptomyces gal* operon such as a defective P1 promoter, P2 promoter, galT gene, galK gene and/or galE gene. Thus, a recombinant DNA molecule (comprising the *Streptomyces gal* operon and a foreign functional DNA sequence operatively linked thereto), which can be prepared by conventional techniques, can be transformed into an appropriate host mutant by conventional techniques for incorporation into the host genome by homologous recombination to enable regulatable expression of the foreign functional DNA sequence without the need of maintaining an expensive antibiotic selection. Such operon may therefore also be incorporated on recombinant DNA expression vectors for regulatable expression of a foreign functional DNA sequence operatively linked to such operon in an appropriate host mutant transformed with such vector without the need of maintaining an expensive antibiotic selection. Such operon is also useful for transforming those cells, viruses and microorganisms, such as strains of Streptomyces, other actinomycetes, and other prokaryotic organisms, such as gal⁻ *E. coli* strains, which do not utilize galactose into galactose utilizing strains. Such transformation may have pleiotrophic effects on the transformed host. By the term "functional DNA sequence" is meant any discrete region of DNA derived directly or indirectly form Streptomyces or any other source which functions in a host organism transformed therewith as a gene expression unit, structural gene, promoter or a regulatory region. Preferred functional DNA sequences include those coding for polypeptides of pharmaceutical importance, such as, but not limited to, insulin, growth hormone, tissue plasminogen activator, alpha-1-anti-trypsin or antigens used in vaccine production. By the term "foreign functional DNA sequence" is meant a functional DNA sequence not derived from the *Streptomyces gal* operon coding region.

This invention also relates to a recombinant DNA molecule comprising the *Streptomyces gal* operon P2 promoter expression unit or any functional derivative thereof. By the term "P2 promoter expression unit" is means that region of the *Streptomyces gal* operon comprising the *Streptomyces gal* operon P2 promoter, galE and galK structural genes and any other regulatory regions required for transcription and translation of such structural genes. By "functional derivative" is meany any derivative of the *Streptomyces gal* operon P2 promoter expression unit which functions in substantially the same was as the naturally occurring region in terms of production of the *Streptomyces gal* operon galE and galK gene products. Such derivatives include partial sequences of the *Streptomyces gal* operon P2 promoter expression unit coding sequence. Techniques for effecting such modification are known in the art, and some have been outlined above. The naturally occurring *Streptomyces gal* operon P2 promoter expression unit can be isolated from the naturally occurring *Streptomyces gal* operon by conventional techniques. The *Streptomyces gal* operon P2 expression unit is useful as a selection marker in an appropriate host mutant and for providing regulatory elements. By "appropriate host mutant" is meant a host which does not utilize galactose because it contains a defect within a homologous structural gene or regulatory region comprised by the Streptomyces P2 promoter expression unit such as a defective P2 promoter, galE gene and/or galK gene. Thus, a recombinant DNA molecule (comprising the *Streptomyces gal* operon P2 promoter expression unit and a foreign functional DNA sequence operatively linked thereto), which can be prepared by conventional techniques, can be transformed into an appropriate host mutant by conventional techniques for incorporation into the host genome by homologous recombination to enable constitutive expression of the foreign functional DNA sequence without the need of maintaining an expensive antibiotic selection. Such expression unit may also be incorporated on recombinant DNA expression vectors for constitutive expression of foreign functional DNA sequences. The *Streptomyces gal* operon P2 promoter expression unit is also useful for complementation of an appropriate host mutant which can then be used for constitutive expression of a foreign functional DNA sequence operatively linked to such expression unit in an appropriate host mutant transformed with such vector without the need of maintaining an expensive antibiotic selection.

This invention also relates to a recombinant DNA molecule comprising the *Streptomyces gal* operon P1 promoter regulated region or any regulatable and functional derivative thereof. By the term "P1 promoter regulated region" is meant that region of the *Streptomyces gal* operon comprising the *Streptomyces gal* operon P1 promoter, galT, galE and galK structural genes and any other regulatory regions required for transcription and translation of such structural genes. By "regulatable and functional derivative" is meant any derivative of the *Streptomyces gal* operon P1 promoter regulated region which functions in substantially the same way as the naturally occurring region in terms of regulatable production of the *Streptomyces gal* operon galT, galE and galK gene products. Such derivatives include partial sequences of the *Streptomyces gal* operon P1 promoter regulated region, as well as derivatives produced by modification of the *Streptomyces gal* operon P1 promoter required region coding sequence. Techniques for effecting such modifications are known in the art, and some have been outlined above. The naturally occurring *Streptomyces gal* operon P1 promotor regulated region can be isolated from the naturally occurring *Streptomyces gal* operon by conventional techniques, such as by excising the P2 promoter from the naturally occurring *Streptomyces gal* operon or inactivating the P2 promoter by a point mutation or by inserting a foreign DNA sequence within the promoter. The *Streptomyces gal* operon P1 promoter regulated region is useful for the utilities outlined above for the *Streptomyces gal* operon.

This invention also relates to a recombinant DNA molecule comprising the *Streptomyces gal* operon P2 promoter or any functional derivative thereof. By "functional derivative" is meant any derivative of the *Streptomyces gal* operon P2 promoter which functions in substantially the same was as the naturally occurring P2 promoter in terms of enabling the binding of RNA polymerase thereto and transcription of a functional DNA sequence operatively linked to such promoter. Such derivatives include partial sequences of the *Streptomyces gal* operon P2 promoter, as well as derivatives produced by modification of the gal operon P2 promoter coding sequence. Techniques for effecting such modification are known in the art, and some have been outlined above. The naturally occurring *Streptomyces gal* operon P2 promoter can be isolated from the naturally occurring *Streptomyces gal* operon by conventional techniques. A recombinant DNA molecule (comprising the *Streptomyces gal* operon P2 promoter and a foreign functional DNA sequence operatively linked thereto), which can be prepared by conventional techniques, can be transformed into an appropriate host mutant by conventional techniques for incorporation into the host genome by homologous recombination to enable constitutive expression of the foreign functional DNA sequence. The *Streptomyces gal* operon P2 promoter is also useful for incorporation into recombinant DNA expression vectors for constitutive expression of a foreign functional DNA sequence operatively linked thereto in viruses and eukaroyotic or prokaryotic cells or organisms, especially in Streptomyces or other actinomycetes, transformed with such vector.

This invention also relates to a recombinant DNA molecule comprising the *Streptomyces gal* operon P1 promoter or any regulatable and functional derivative thereof. By "regulatable and functional derivative" is meant any derivative of the *Streptomyces gal* operon P1 promoter which functions in substantially the same way as the naturally occurring P1 promoter in terms of enabling the binding of RNA polymerase thereto and regulating the transcription of a functional DNA sequence operatively linked to such promoter. Such derivatives include partial sequences of the *Streptomyces gal* operon P1 promoter, as well as derivatives produced by modification of the gal operon P1 promoter coding sequence. Techniques for effecting such modification are known in the art, and some have been outlined above. The naturally occurring *Streptomyces gal* operon P1 promoter can be isolated from the naturally occurring *Streptomyces gal* operon by conventional techniques. A recombinant DNA molecule (comprising the *Streptomyces gal* operon P1 promoter and a foreign functional DNA sequence operatively linked thereto), which can be prepared by conventional techniques, can be transformed into an appropriate host mutant by conventional techniques for incorporation into the host genome by homologous recombination to enable regulatable expression of the foreign functional DNA sequence. The *Streptomyces gal* operon P1 promoter is also useful for incorporation into recombinant DNA expression vectors for regulatable expression of a foreign functional DNA sequence operatively linked thereto in viruses and eukaroyotic or prokaryotic cells or organisms, especially Streptomyces or other actinomycetes, transformed with such vector.

This invention also related to a recombinant DNA molecule comprising the *Streptomyces gal* operon galE, galT or galK gene, or any functional derivative thereof. By "functional derivative" is meant any derivative of the *Streptomyces gal* operon galE, galT or galK gene which functions in substantially the same way as the naturally occurring gene in terms of production of an active galE, galT, or galK type gene product. Such derivatives include partial sequences of the *Streptomyces gal* operon galE, galT, or galK gene, as well as derivatives produced by modification of the gal operon sequence. Techniques for effecting such modifications are known in the art, and some have been outlined above. The naturally occurring *Streptomyces gal* operon galE, galT and/or galK gene can be isolated from the naturally occurring *Streptomyces gal* operon by conventional techniques. The *Streptomyces gal* operon galE, galT and/or galK gene can be used as a selection marker in an appropriate host mutant. By "appropriate host mutant" is meant a host which does not utilize galactose because it contains a defect within a homologous galE, galT and/or galK gene. Thus, a recombinant DNA molecule (comprising the *Streptomyces gal* operon galE, galT and/or galK gene and a foreign functional DNA sequence, both of which are operatively linked to appropriate regulatory region). which can be prepared by conventional techniques can be transformed into an appropriate host mutant by conventional techniques for incorporation into the host genome by homologous recombination to enable detection of transformants without the need of maintaining an expensive antibiotic selection. Likewise, a recombinant DNA vector comprising the *Streptomyces gal* operon galE, galT and/or galK gene and a foreign functional DNA sequence, both of which are operatively linked to appropriate regulatory regions, as well as a replicon, can be transformed into an appropriate host mutant by conventional techniques to enable detection of transformants without the need of maintaining an expensive antibiotic selection. The *Streptomyces gal* operon galE, galK and/or galT gene is also useful for complementation of an appropriate host mutant.

The *Streptomyces gal* operon galE gene is also useful for providing a ribosome binding site and initiation codon which can be fused to a foreign functional DNA sequence to enable the expression of such coding sequence when incorporated into an appropriate expression vector and transformed into an appropriate host. If such foreign functional DNA sequence is fused to the galE gene ribosome binding site and initiation codon in a recombinant DNA expression vector comprising the *Streptomyces gal* operon P2 promoter expression unit, or the entire gal operon, such DNA sequence will be constitutively expressed when such vector is transformed into an appropriate host organism. If such DNA sequence is fused to the galE gene ribosome binding site and initiation codon in a recombinant DNA expression vector comprising the *Streptomyces gal* operon P2 promoter regulated region, expression of such DNA sequence can be regulated when such vector is transformed into an appropriate host organism by controlling the presence or absence of galactose or glucose.

The *Streptomyces gal* operon galT gene is also useful for providing a ribosome binding site and initiation codon which can be fused to a foreign functional DNA sequence to enable the expression of such coding sequence when incorporated onto an appropriate expression vector and transformed into an appropriate host. If such DNA sequence is fused to the galT gene ribosome binding site and initiation codon in a recombinant DNA expression vector comprising the *Streptomyces gal* operon P1 promoter regulated region, or the entire gal operon, expression of such coding sequence can be regulated in a host transformed with such vector as outlined above.

This invention also relates to a recombinant DNA vector comprising a replicon, *Streptomyces gal* operon, or a functional and regulatable derivative thereof, and a foreign functional DNA sequence operatively linked to such operon. Such vector can be prepared by conventional techniques. The replicon employed should be one known for its ability to stably and extrachromosomally, maintain a vector in the host organism which is to be the host transformed with the vector.

This invention also relates to a transformed host microorganism comprising a recombinant DNA vector wherein said vector contains a replicon, the *Streptomyces gal* operon, or a functional and regulatable derivative thereof, and a foreign functional DNA sequence operatively linked to such operon; and to the method of preparing such host which comprises transforming an appropriate host microorganism with such vector. Appropriate host microorganisms which may be employed in the method of this invention include viruses, and eukaroyotic and prokarylotic cells or organisms, especially actinomycetes, such as those of the genes Streptomyces. The most preferred host microorganisms belong to the genus Streptomyces. Preferred species of Streptomyces include *Streptomyces lividans, S. coelicolor, S. azuraeus* and *S. albus*. Transformation of such host microorganism with such vector can be accomplished using conventional techniques such as the method of Chater et al., *Curr. Top. Micro. Imm.*, 96, 69–95 (1982). This invention also related to a method of expressing the functional DNA sequence contained by such transformed host of this invention which comprises cultivating such transformed host under suitable conditions such that the functional DNA sequence is expressed. By "suitable conditions" is meant those conditions which will allow the host to grow and which enable the expression of the functional DNA sequence. Such suitable conditions can be determined by one of skill in the art using conventional techniques and will depend on various factors, such as the host organism employed and the functional DNA sequence to be expressed. This invention is also related to a method of regulating the expression of the functional DNA sequence contained by such transformed host which comprises cultivating a transformed host containing such functional DNA sequence under appropriate conditions such that its expression is regulatable. By "appropriate conditions" is meant those conditions which enable the *Streptomyces gal* operon (and thus the foreign functional DNA sequence) to be regulatable. By "regulatable" is meant responsive to the presence of galactose or its metabolites and the presence f glucose or its metabolites in the growth media of the transformed host cell. Such regulation can be carried out by addition or deletion of galactose or glucose to the transformed host's culture medium. The optimal elvels of galactose and/or glucose for up or down-regulation of the expression of the foreign functional DNA coding sequence by the transformed host of this invention can be readily determined by one of skill in the art using conventional techniques.

This invention also related to a recombinant DNA vector comprising a replicon, a *Streptomyces gal* operon P2 promoter expression unit, or a functional derivative thereof, and a foreign functional DNA sequence operatively linked to such unit. Such a vector can be prepared by conventional techniques. The replicon employed should be one known for its ability to stably, and extra-chromosomally, maintain a vector in the host organism which is to be transformed with the vector.

This invention also relates to a transformed host microorganism comprising a recombinant DNA vector wherein said vector contains a replicon, the *Streptomyces gal* operon P2 promoter expression unit, or a functional derivative thereof, and a foreign functional DNA sequence operatively linked to such unit and to the method of preparing such host which comprises transforming an appropriate host microorganism with such vector. By the term "operatively linked" is meant that a functional DNA sequence is transcriptionally or translationally linked to an expression control sequence (i.e., the *Streptomyces gal* operon P2 promoter expression unit, P1 promoter regulated region, P1 promoter or P2 promoter) in such a way so that the expression of the functional DNA sequence can be transcriptionally or translationally linked to the *Streptomyces gal* operon by inserting such operon within the *Streptomyces gal* operon P1 or P2 promoter transcript. By the term "replicon" is meant that region of DNA on a plasmid which functions to maintain, extrachromosomally, such plasmid is a host microorganism or cell transformed therewith. It has also been discovered that the *Streptomyces gal* operon, and smaller portions thereof, is useful as a nucleic acid probe to obtain homologous sequences from other cells and organisms. Appropriate host microorganisms which may be employed in the method of this invention include any virus or eukaroyotic or prokaryltic cell or organism, especially any actinomycetes such as those of the genes Streptomyces. The most preferred host microorganisms belong to the genus Streptomyces. Preferred species of Streptomyces include *Streptomyces lividans, S. coelicolor, S. azuraeus* and *S. albus*. Transformation of such host microorganism with such vector can be accomplished using conventional techniques such as the method of Chater et al., *Curr. Top. Micro. Imm.*, 96, 69–95 (1982). This invention relates to a method of expressing the functional DNA sequence contained by such transformed host of this invention which comprises cultivating such transformed host under suitable conditions such that the functional DNA sequence is expressed. By "suitable conditions" is meant those conditions which will allow the host to grow and which enable the expression of the functional DNA sequence. Such suitable conditions can be determined by one of skill in the art using conventional techniques and will depend on various factors, such as the host organism employed and the functional DNA sequence to be expressed.

This invention also related to a recombinant DNA vector comprising a replicon, a *Streptomyces gal* operon P1 promoter regulated region, or a functional and regulatable derivative thereof, and a foreign functional DNA sequence operatively linked to such region. Such a vector can be prepared by conventional techniques. The replicon employed should be one known for its ability to stable and extrachromosomally maintain a vector in the host or organism which is to be the host transformed with the vector.

This invention also related to a transformed host microorganism comprising a recombinant DNA vector wherein said vector contains a replicon, a *Streptomyces gal* operon P1 promoter regulated region, or a functional and regulatable derivative thereof, and a foreign functional DNA sequence operatively linked to such region; and to the method of preparing such host which comprises transforming an appropriate host microorganism with such vector. Appropriate host microorganisms which may be employed include any virus or eukaroyotic or prokaryotic cell or organism especially actinomycetes such as those of the microorganisms belong to the genus Streptomyces. Preferred species of Streptomyces include *Streptomyces lividans, S. coelicolor, S. azuraeus* and *S. albus*. Transformation of such host microorganisms with such vector can be accomplished using conventional techniques such as the method of Chater et al., *Curr. Top. Micro. Imm.*, 96, 69–95 (1982). This invention also related to a method of expressing the foreign functional DNA sequence contained by such transformed host of this invention which comprises cultivating such transformed host under suitable conditions such that the functional DNA sequence is expressed. By "suitable conditions" is meant those conditions which will allow the host to grow and which enable the expression of the function DNA sequence. Such suitable conditions can be determined by one of skill in the art using conventional techniques and will depend on various factors, such as the host organism employed and the functional DNA sequence to be expressed. This invention also related to a method of regulating the expression of the functional DNA sequence contained by such transformed host which comprises cultivating a transformed host containing such functional DNA sequence under appropriate conditions such that its expression is regulatable. By "appropriate conditions" is meant those conditions which enable the *Streptomyces gal* operon P1 promoter regulated region (and thus the foreign functional DNA sequence) to be regulatable. By "regulatable" is meant responsive to the presence or absence of galactose or its metabolites and the presence or absence of glucose or its metabolites in the growth media or the transformed host cell. Such regulation can be carried out by addition or deletion of galactose or glucose to the transformed host's culture medium.

The invention also relates to a recombinant DNA vector comprising a replicon, a *Streptomyces gal* operon P2 promoter, or a functional derivative thereof, and a foreign functional DNA sequence operatively linked to such promoter. Such a vector can be prepared by conventional techniques. The replicon employed should be one known for its ability to stably and extrachromosomally maintain a vector in the host organism which is to be the host transformed with the vector.

This invention also relates to a transformed host microorganism comprising a recombinant DNA vector wherein said vector contains a replicon, a *Streptomyces gal* operon P2 promoter, or a functional derivative thereof, and a foreign functional DNA sequence operatively linked to such region; and to the method of preparing such host which comprises transforming an appropriate host microorganism with such vector. Appropriate host microorganisms which may be employed include actinomycetes such as those of the genus Streptomyces. The most preferred host microorganisms belong to the genus Streptomyces. Preferred species of Streptomyces include Streptomyces lividans, S. coelicolor, S. azuraeus and *S. albus.* Transformation of such host microorganism with such vector can be accomplished using conventional techniques such as the method of Chater el al., *Curr. Top. Micro. Imm.*, 96, 69–95 (1982). This invention also relates to a method of expressing the foreign functional DNA sequence contained by such transformed host of this invention which comprises cultivating such transformed host under suitable conditions such that the functional DNA sequence is expressed. By "suitable conditions" is meant those conditions which will allow the host to grow and which enable the expression of the functional DNA sequence. Such suitable conditions can be determined by one of skill in the art using conventional techniques and will depend on various factors, such as the host organism employed and the functional DNA sequence to be expressed.

This invention also relates to a recombinant DNA vector comprising a replicon, *Streptomyces gal* operon P1 promoter, or any regulatable and functional derivative, therefore, and a foreign functional DNA sequence operatively linked to such region. Such a vector can be prepared by conventional techniques. The replicon employed should be one known for its ability to stably and extrachromosomally maintain a vector in the host organism which is to be the host transformed with the vector.

This invention also relates to a transformed host microorganism comprising a recombinant DNA vector wherein said vector contains a replicon, the *Streptomyces gal* operon P1 promoter, or any regulatable and functional derivative thereof, and a foreign functional DNA sequence operatively linked to such region; and to the method of preparing such host which comprises transforming an appropriate host microorganism with such vector. Appropriate host microorganisms which may be employed include viruses or prokaryotic or eukaroyotic cells or organisms, especially actinomycetes such as those of the genus Streptomyces. The most preferred host microorganisms belong to the genus Streptomyces. Preferred species of Streptomyces include *Streptomyces lividans, S. coelicolor, S. azuraeus* and *S. albus.* Transformation of such host microorganism with such vector can be accomplished using conventional techniques such as the method of Chater et al., *Curr. Top. Micro. Imm.*, 96, 69–95 (1982). This invention also relates to a method of expressing the foreign functional DNA sequence contained by such transformed host of this invention which comprises cultivating such transformed host under suitable conditions such that the functional DNA sequence is expressed. By "suitable conditions" is meant those conditions which will allow the host to grow and which enable the expression of the functional DNA sequence. Such suitable conditions can be determined by one of skill in the art using conventional techniques and will depend on various factors, such as the host organism employed and the foreign functional DNA sequence to be expressed. This invention also relates to a method of regulating the expression of the functional DNA sequence contained by such transformed host which comprises cultivating a transformed host containing such foreign functional DNA sequence under appropriate conditions such that its expression is regulatable. By "appropriate conditions" is meant those conditions which enagle the gal operon P1 promoter (and thus the functional DNA sequence) to the regulatable. By "regulatable" is meant responsive to the presence or absence of galactose or its metabolites and the presence of glucose or its metabolites in the growth media of the transformed host cell. Such regulation can be carried out addition or deletion of galactose or glucose to the transformed host's culture medium.

EXAMPLES

In the following Examples, specific embodiments of the invention are more fully disclosed. These Examples are intended to be illustrative of the subject invention and should not be construed as limiting its scope. In all Examples, temperature is in degrees Centigrade ("C.)

By utilizing conventional methods, such as those outlined in the following Examples, one of skill in the art can isolate the gal operon from any galactose utilizing strain of Streptomyces. Furthermore, by utilizing techniques similar to those employed herein to isolate the *Streptomyces gal* operon, one of skill in the art can attempt to use the *Streptomyces gal* operon to isolate a gal operon from other galactose utilizing other strains of Streptomyces, especially *S. coelicolor, S. azuraeus, S. albus* and other *S. lividans* strains.

Molecular genetic manipulations and other techniques employed in the following Examples are described in Hopwood et al., *Genetic Manipulation of Streptomyces: A Laboratory Manual*, John Innes Foundation, Norwich, England (1985).

ABBREVIATIONS

In the following Examples, the following abbreviations may be employed:

LB: 10 grams (g) tryptone, 5 g yeast extract, 5 g NaCl

MBSM (modified MBSM): See, Brawner et al., *Gene*, 40, 191 (1985)(in press)

MOPS: (3)-N-morpholino-(proprane-sulfonic acid)

YEME+MgCL$_2$+Glycine: [per liter(1)] 3 g yeast extract, 5 peptone, 3 g malt extract, 10 g glucose, 10 g MgCL$_2$"62H$_2$O, 340 g sucrose.

SL: Mix together (NH$_4$)$_2$SO$_4$(1 g/l); L-asparagine (2 g/l); K$_2$HPO$_4$ (9 g/l); NaH$_2$PI$_4$ (1 g/l) for 0.2% agar and autoclave. Then mix with yeast extract (20 g/l), MgCl$_2$ (5 g/l); CuCl$_2$ (0.1 g/l); Trace elements [20 ml/1—include ZnCl$_2$—40 mg/l); FeCl$_3$"6H$_2$O (200 mg/l); CuCl$_2$"2H$_2$O (10 mg/l); NaB$_4$O$_7$"10H$_2$O (10 mg/l); (NH$_4$)$_6$MO$_7$O$_{24}$"4H$_2$O (10 mg/l )] filter and sterilize.

YEME (Ym base): (per liter) yeast extract (3 g); peptone (5 g); malt extract (3 g); MgCl$_2$"6H$_2$O (2 g)

Ymglu: YEME+glucose (10 g)

Ymgal: YEME+galactose (10 g)

BACTERIAL STRAINS

In the following Examples, the following strains of *E. coli* are employed;

| CGSC Strain #(a) | Strain Designation | Sex | Chromosomal Markers |
| --- | --- | --- | --- |
| 4473 (galE⁻) | W3109 F⁻ | galE9,(b) g⁻, | IN(rrnD-rrnE)1 |
| 4467 (galT⁻) | W3101 F⁻ | galT22(b) g⁻; | IN(rrnD-rrnE)1 |
| 4498 (galE⁻) | PL-2 Hfr thi-1, | relA1, 921E28, g⁻, | spoT1 |

(a)CGSC Strain # is the stock number designated for such strain by the *E. coli* Genetic Stock Center of the Department of Human Genetics, Yale University School of Medicine, 333 Cedar Street, P.O. Box 3333, New Haven, Connecticut, 06510,U.S.A.

(b)galE9 is the old Lederberg gal9; galT22 is the old Lederberg gal1.

S1 ANALYSIS

S1 analysis is used to identify the 5' end of RNAs and the length of a RNA of interest. In the following Examples, S1 analysis refers to S1 experiments carried out according to the method of Weaver et al., *Nucl. Acids Res.*, 7, 1175 (1979) and Berk et al., *Proc. Natl. Acad. Sci. USA*, 75, 1214 (1978).

EXAMPLE I

A. Cloning of a *Streptomyces Lividans* Galactokinase Gene

*Streptomyces lividans* strain 1326 is described by Bibb et al., *Mol. Gen. Genetics*, 184, 230-240 (1981) and was obtained from D. A. Hopwood, John Innes Foundation, Norwich, England. *Streptomyces lividans* strain 1326 and *S. lividans* strain 1326 containing the pIJ6 plasmid were deposited in the Agricultural Research Culture Collection, See, Adams et al., *Biochem. Biophys. Res. Comm.*, 89(2), 650-58 (1979)] with 30 mg/ml chloramphenicol. Twenty plates were spread with approximately 200 transformants per plate. After three days incubation at 37° C., no transformants were detected. The minimal plates were then sprayed with nicotinic acid to 5 ug/ml to supplement the nicotinic acid requirement of *E. coli* strain K21, and the incubation was continued for 3 more days at 37° C. and for 2 additional days at room temperature. After such incubation, the surviving colonies were patched to both MacConkey galactose agar (MAC-GAL) [See, Miller et al., cited above ] with 30 ug/ml chloramphenicol and to M63 minimal agar [See, Miller et al., cited above] supplemented with 0.5% galactose, 5 ug/ml nicotinic acid, 5 ug/ml thiamine and 30 ug/ml chloramphenicol. Only two colonies contained cosmid DNA that transformed *E. coli* K21 to a galK+ phenotype. Such cosmids were designated as psLIV-GAL-1 and pSLAIVAG-2. Both colonies were light red on MAC-GAL (i.e., they were galK+) and also grew on the M63 medium.

Plasmid pSLIVGAL-1 and PSLIVGAL-2 were isolated from the two galK+ colonies described above and were transformed, according to the method of Chater et al., *Curr. Top. Micro. Inn.*, 96, 69-95 (1982), into *Streptomyces lividans* strain 1326-12 K (a galK deficient strain isolated after UV mutagenesis of *S. lividans* strain 1326, See, Brawner et al., *Gene*, 40, 191 (1985), (in press). Plasmid encoded complementation of the *S. lividans* 1326-12K (galK⁻) host was tested by observing growth of spores plated on MBSM-gal-thiostrepton according to the method of Brawner et al., *Gene*, 40, 191 (1985) (in press). pSLIVGAL-2 showed no detectable complementation of the Streptomyces 1326-12K host.

Cell extracts were prepared from cultures grown in SL medium supplemented with 1% glucose or galactose and 10 ug/ml thiostrepton. The extracts were analyzed for galactokinase production by immunoblot analysis (see, Brawner et al., *Gene*, 40, 191 (1985), in press) using rabbit antisera prepared against *E. coli* galactokinase. The protein detected by immunoblot analysis was the approximate size of *E. coli* galK. Such protein appears in galactose supplemented cultures of Streptomyces at levels several fold higher than in glucose cultures.

B. Mapping of the *S. Lividans* GalK Region Within a Cosmid

The galK region of the pSLIVGAL-1 and pSLIV-GAL2 cosmids, prepared as described above, was identified by cloning random fragments from the cosmids into a pUC18 derivative [See, Norrander et al., *Gene*, 26, 101-106 (1983)] and scoring complementation of *E. coli* strain MM294 (galK⁻) on MAC-GAL medium. The cosmid clone was partially digested with Sau3AI (using conditions which maximized the yield of 2 to 4 kilobase fragments), and the products of this reaction were ligated into the BglII site of pUC18-TT6, a derivative of pUC18 constructed by insertion of the following synthetic DNA sequence into the BamHI site of pUC18:

5'GATCAGATCTTGATCACTAGCTAGCTAG 3'
3' TCTAGAACTAGTGATCGATCGATCCTAG 5'

Twelve galK+ clones (red on MAC-GAL) were screened for size. One clone, designated as plasmid pSAU10, was the smallest and had an insert size of approximately 1.4 Kb.

In contrast to colonies containing pSLIVGAL1, the pUC clones were very red on MAC-GAL medium, indicating and increased production of galactokinase. The most likely explanation for the increased enzyme level was that the *S. lividans* galK gene was now being transcribed by an *E. coli* promoter which was stronger than the upstream promoter on the cosmid.

The insert of pSAU10 was isolated as an EcoRI to HindIII fragment (these sites flank the insert region of pUC18-TT6) for use as a probe for the *S. lividans* galK gene. The chromosomal DNA used in the cloning was restricted with EcoRI plus MluI and BamHI plus BglII, and then blotted according to the method of Southern, *J. Mol. Biol.*, 98, 503 (1975). The pSAU10 fragment was nick translated and hybridized to the blot. The probe identified a 1.3 kb EcoRI-MluI fragment and a 5 kb BamHI-BalII fragment in the chromosomal digests. When this data was compared to the map of the cosmid insert, the location of the galK gene (between map positions 5 and 7, See Table A) was confirmed.

C. DNA Sequencing of the *S. Lividans* Gal Operon

The *Streptomyces lividans* gal operon was sequenced by chain termination [(See, Sanger et al., *Proc. Nat'l Acad. Sci., U.S.A.*, 65, 499 (1980)]. The initial sequences of galK were derived from Sau3AI and SalI fragments of the insert of pSAU6 (a 2.3 Kb sibling of pSAU10) shotgun cloned into the BamHI and SalI sites (respectively) of M13 mp 10 [See, Messing, *Methods in Enzymology*, 101, 20 (1983)]. Amino acid sequences of *S. lividans galT, galE and galK* genes were predicted by computer, and further analyzed by comparison with amino acid sequences of the *E. coli* and or *S. cerevisiae* galactokinase, gal-1-phosphate uridyltransferase and UDP-4-epimerase enzymes. The sequences of these proteins were predicted by computer analysis using the total or partial DNA sequence of the genes which encode the gal enzymes [See, Debouck et al., *Nuc Acids. Res.*, 13(6), 1841-1853 (1985), and Citron and Donelson, *J. Bacteriology*, 158, 269 (1984)]. Some homology was found between the inferred protein sequence for the *S. lividans* galK, galT, galE gene products and their respective *E. coli* and/or *S. cerevisiae* gene products.

The complete DNA sequence of the *S. lividans* gal operon is shown in Table 1. Includes in Table 1 are the transcription start sites for the operon's promoters and the predicted amino acid sequences of the galT, galE and galK products.

TABLE 1

TRANSLATED SEQUENCE OF *STREPTOMYCES LIVIDANS* GALACTOSE OPERON

```
    -120      -110      -100      -90       -80       -70
CTA CGC CTC CGC GTT CAG TAA TTG AAC ACT TTT GGT GAT GAA CTT TGT
TTG ATT GTG

-60       -50       -40       -30  -20
ATG TGA CAG GGG GGT GGT GGT GGG TTG TGA TGT GTT ATG TTT GAT TGT
GTT GGA TGA TTG
                                   galP1

-10       1         10        20        30   40
ACG GGC GTC CTG GTG ACT CAT GGG TGG GTG CAG AGG AGT GCG GCA GTG
AAG AAG ACC

Met Thr His Gly Trp Val Gln Arg Ser Ala Ala Val Lys Lys Thr
         galT 50             60   70   80        90        100
TCG ACC CGG CTG GCC GAC GGC CGT GAG CTG GTC TAC TAC GAC CTG CGC
GAC GAC ACC Ser Thr Arg Leu Ala Asp Gly Arg Glu Leu Val Tyr Tyr Asp Leu Arg Asp Asp Thr 110       120       130       140       150
GTG CGC GAC GCC GTG GAC CGC CGT CCG CTG GAG CGG ACC GTC ACC ACG
TCC GAG GTG Val Arg Asp Ala Val Asp Arg Arg Pro Leu Glu Arg Thr Val Thr Thr Ser Glu Val 160       170       180       190       200       210
CGA CGC GAC CCG CTG CTC GGC GAC TCC GCG CCG TCG CGC CTC GCA CCG
GCA GGG GCG Arg Arg Asp Pro Leu Leu Gly Asp Ser Ala Pro Ser Arg Leu Ala Pro Ala Gly Ala 220       230       240       250       260       270
CAC CTA CCA TCC GCC GGC CGA CCA GTG CCC GCT GTG CCc GTC GGA CGG
GGA ACG GCT His Leu Pro Ser Ala Gly Arg Pro Val Pro Ala Val Pro Val Gly Arg Gly Thr Ala 280       290       300       310       320       330
GAG CGA GAT CCG GCC TAT GAC GTG GTG GTC TTC GAG AAT CGC TTT CCC
TCG CTG GCC Glu Arg Asp Pro Ala Tyr Asp Val Val Val Phe Glu Asn Arg Phe Pro Ser Leu Ala
```

TABLE 1-continued
TRANSLATED SEQUENCE OF *STREPTOMYCES LIVIDANS* GALACTOSE OPERON

```
      340       350       360       370       380
       •         •         •         •         •
GGT GAC TCC GGG CGC TGC GAG GTC GTC TGC TTC ACC TCC GAC CAC GAC
GCC TCC TTC
Gly Asp Ser Gly Arg Cys Glu Val Val Cys Phe Thr Ser Asp His Asp Ala Ser Phe 390       400       410       420       430       440
 •         •         •         •         •         •
GCC GAC CTG AGC GAG GAC CAG GCC CGG CTG GTC GTC GAC GCC TGG ACG
GAC CGC ACC
Ala Asp Leu Ser Glu Glu Gln Ala Arg Leu Val Val Asp Ala Trp Thr Asp Arg Thr 450       460       470       480       490       500
      •         •         •         •         •         •
TCC GAG CTG TCC CAT CTG CCC TCC GTT GAA CAG GTG TTC TGC TTC GAG
AAC CGG GGC
Ser Glu Leu Ser His Leu Pro Ser Val Glu Gln Val Phe Cys Phe Glu Asn Arg Gly 510       520       530       540       550
         •         •         •         •         •
GCC GAC ATC GGG GTG ACG CTG GGT CAC CCG CAC GGG CAG ATC TAC GCC
TAC CCG TTC
Ala Glu Ile Gly Val Thr Leu Gly His Pro His Gly Gln Ile Tyr Ala Tyr Pro Phe 560       570       580       590       600       610
 •         •         •         •         •         •
ACC ACC CCC CGC ACC GCC CTG ATG CTC CGT TCA CTC GCC GCC CAC AAG
GAC GCG ACG
Thr Thr Pro Arg Thr Ala Leu Met Leu Arg Ser Leu Ala Ala His Lys Asp Ala Thr 620       630       640       650       660       670
     •         •         •         •         •         •
GGC GGG GGG AAC CTG TTC GAC TCC GTG CTG GAG GAG GAG CTG GCC GGT
GAG CGG GTC
Gly Gly Gly Asn Leu Phe Asp Ser Val Leu Glu Glu Glu Leu Ala Gly Glu Arg Val 680       690       700       710       720
        •         •         •         •         •
GTC CTG GAG GGT GAG CAC TGG GCC GCC TTC GTC GCG TAC GGC GCG CAC
TGG CCG TAC
Val Leu Glu Gly Glu His Trp Ala Ala Phe Val Ala Tyr Gly Ala His Trp Pro Tyr 730       740       750       760       770       780
 •         •         •         •         •         •
GAG GTG CAC CTC TAC CCG AAG CGG CGG GTG CCC GAT CTG CTC GGG CTC
GAC GAG GCG
Glu Val His Leu Tyr Pro Lys Arg Arg Val Pro Asp Leu Leu Gly Leu Asp Glu Ala 790       800       810       820       830       840
 •         •         •         •         •         •
GCT CGC ACA GAA TTC CCC AAG GTC TAC CTG GAG CTG CTG AGG CGT TTC
GAC CGG ATC
Ala Arg Thr Glu Phe Pro Lys Val Tyr Leu Glu Leu Leu Arg Arg Phe Asp Arg Ile 850       860       870       880       890       900
      •         •         •         •         •         •
TTC GGC GAG GGC GAG CCC CCG ACC CCC TAC ATC GCG GCC TGG CAC CAG
GCG CCG TTC
Phe Gly Glu Gly Glu Pro Pro Thr Pro Tyr Ile Ala Ala Trp His Gln Ala Pro Phe 910       920       930       940       950
         •         •         •         •         •
GGG CAG CTG GAG TTC GAG GGT GTG ACG CGC GAC GAC TTC GCG CTC CAC
CTG GAA CTT
Gly Gln Leu Glu Phe Glu Gly Val Thr Arg Asp Asp Phe Ala Leu Lis Leu Glu Leu 960       970       980       990      1000      1010
 •         •         •         •         •         •
TTC ACT TCC GCC GTA CGT CCG GCA AGC TGA AGT CCC TCG CGG GCT CCG
AAT CCG GCA
Phe Thr Ser Ala Val Arg Pro Ala Ser — galP2

1020     1030      1040     1050      1060      1070
    •         •         •        •         •         •
 TGAACGTGTTCATCAACGACGTACCCCCGGAGCGCGCGGCCGAGCG
ACTGCGAGAGGTAGCGAG
```

TABLE 1-continued
TRANSLATED SEQUENCE OF *STREPTOMYCES LIVIDANS* GALACTOSE OPERON

```
      1080      1090      1100      1110      1120      1130
        *         *         *         *         *         *
TTC ATG AGC GGG AAG TAC CTG GTG ACA GGT GGT GCC GGA TAC GTC GGC
AGC GTC GTC
 Met Ser Gly Lys Tyr Leu Val Thr Gly Gly Ala Gly Tyr Val Gly Ser Val Val
 galE 1140      1150      1160      1170      1180      1190
          *         *         *         *         *         *
GCC CAG CAC TTG GTG GAG GCG GGG AAC GAG GTC GTG GTG CTG CAC AAT
CTG TCG ACC
Ala Gln His Leu Val Glu Ala Gly Asn Glu Val Val Val Leu His Asn Leu Ser Thr 1200      1210      1220      1230      1240
              *         *         *         *         *
GGC TTC CGT GAG GTG TGC CGG CGG GTG CCT CGT TCG TCG AGG CGA CAT
CCG GGA CGC
Gly Phe Arg Glu Val Cys Arg Arg Val Pro Arg Ser Ser ARg Arg His Pro Gly Arg 1250      1260      1270      1280      1290      1300
   *         *         *         *         *         *
CGC CAA GTG CGT GGA CGG CTC TCG TTC GAC GGC GTG CTG CAC TTC GCC
GCC TTC TCC
Arg Gln Val Arg Gly Arg Leu Ser Phe Asp Gly Val Leu His Phe Ala Ala Phe Ser 1310      1320      1330      1340      1350      1360
    *         *         *         *         *         *
CAG GTC GGC GAG TCG GTC GTG AAG CCC GAG AAG TAC TGG GAC AAC AAC
GTC GGT GGC
Gln Val Gly Glu Ser Val Val Lys Pro Glu Lys Tyr Trp Asp Asn Asn Val Gly Gly 1370      1380      1390      1400      1410      1420
       *         *         *         *         *         *
ACC ATG GCG CTG CTG GAG GCC ATG CGG GGC GCG GGT GTG CGG CGG CTC
GTC TTC TCC
Thr Met Ala Leu Leu Glu Ala Met Arg Gly Ala Gly Val Arg Arg Leu Val Phe Ser 1430      1440      1450      1460      1470
          *         *         *         *         *
TCC ACG GCC GCC ACG TAC GGC GAG CCC GAG CAG GTT CCC ATC GTC GAG
TCC GCG CCG
Ser Thr Ala Ala Thr Tyr Gly Glu Pro Glu Gln Val Pro Ile Val Glu Ser Ala Pro 1480      1490      1500      1510      1520      1530
   *         *         *         *         *         *
ACG AGG CCC ACC AAT CCG TAC GGC GCC TCG AAG CTC GCC GTC GAC CAC
ATG ATC ACC
Thr Arg Pro Thr Asn Pro Tyr Gly Ala Ser Lys Leu Ala Val Asp His Met Ile Thr 1540      1550      1560      1570      1580      1590
      *         *         *         *         *         *
GGC GAG GCG GCG GCC CAC GGG CTG GGC GCG GTC TCC GTG CCG TAC TTC
AAC GTC GCG
Gly Glu Ala Ala Ala His Gly Leu Gly Ala Val Ser Val Pro Tyr Phe Asn Val Ala 1600      1610      1620      1630      1640
             *         *         *         *         *
GGC GCG TAC GGG GAG TAC GGC GAG CGC CAC GAC CCC GAG TCG CAT CTG
ATT CCG CTG
Gly Ala Tyr Gly Glu Tyr Gly Glu Arg His Asp Pro Glu Ser His Leu Ile Pro Leu 1650      1660      1670      1680      1690      1700
   *         *         *         *         *         *
GTC CTT CAA GTG GCG CAG GGC AGG CGG GAG GCC ATC TCC GTC TAC GGC
GAC GAC TAC
Val Leu Gln Val Ala Gln Gly Arg Arg Glu Ala Ile Ser Val Tyr Gly Asp Asp Tyr 1710      1720      1730      1740      1750      1760
    *         *         *         *         *         *
CCG ACG CCG GAC CGA CCT GTG TGC GCG ACT ACA TCC ACG TCG CCG ACC
TGG CCG AGG
Pro Thr Pro Asp Arg Pro Val Cys Ala Thr Thr Ser Thr Ser Pro Thr Trp Pro Arg
```

TABLE 1-continued
TRANSLATED SEQUENCE OF *STREPTOMYCES LIVIDANS* GALACTOSE OPERON

```
        1770      1780      1790      1800      1810
         •         •         •         •         •
CCC ACC TGC TGG CCG TGC GCC GCC GCC CCG GGC GAG CAC CTC ATC TGC
AAC CTG GGC
Pro Thr Cys Trp Pro Cys Ala Ala Ala Pro Gly Glu His Leu Ile Cys Asn Leu Gly 1820      1830      1840      1850      1860      1870
    •         •         •         •         •         •
AAC GGC AAC GGC TTC TCC GTC CGC GAG GTC GTC GAG ACC GTG CGG CGG
GTG ACC GGC
Asn Gly Asn Gly Phe Ser Val Arg Glu Val Val Glu Thr Val Arg Arg Val Thr Gly 1880      1890      1900      1910      1920      1930
       •         •         •         •         •         •
CAT CCG ATC CCC GAG ATC ATG GCC CCG CGC CGC GGG CGC GAC CCG GCG
GTC CTG GTC
His Pro Ile Pro Glu Ile Met Ala Pro Arg Arg Gly Arg Asp Pro Ala Val Leu Val 1940      1950      1960      1970      1980      1990
       •         •         •         •         •         •
GCG TCG GCC GGC ACC GCC CGC GAG AAG CTG GGC TGG AAC CCG TCC CGC
GCG GAC CTC
Ala Ser Ala Gly Thr Ala Arg Glu Lys Leu Gly Trp Asn Pro Ser Arg Ala Asp Leu 2000      2010      2020      2030      2040
          •         •         •         •         •
GCC ATC GTG TCG GAC GCG TGG GAG TTG CCG CAG CGG CGC GCG GGC CAG
TAG TA
Ala Ile Val Ser Asp Ala Trp Glu Leu Pro Gln Arg Arg Ala Gly Gln ---

2050      2060      2070      2080      2090      2100
    •         •         •         •         •         •
ACC GCA GTT ACC GGA AAG GCG AGG GGT CAG GGC ATG GGC GAG GCT GTC
GGG GAA CCG
                        Met Gly Glu Ala Val Gly Glu Pro
                        galK 2110      2120      2130      2140      2150
       •         •         •         •         •
TCG GCG AGC GGT TCC GGG AGC TGT ACG GGG CGG AGC CGG AGG GGG TGT
GGG CGC CGA
Ser Ala Ser Gly Ser Gly Ser Cys Thr Gly Arg Ser Arg Arg Gly Cys Gly Arg Arg 2160      2170      2180      2190      2200      2210
  •         •         •         •         •         •
GCG GGC CGG GAG AAC CTC ATC GGG GAG CAC ACC GAC TAC AAC GAC GGC
TTC GTC ATG
Ala Gly Arg Glu Asn Leu Ile Gly Glu His Thr Asp Tyr Asn Asp Gly Phe Val Met 2220      2230      2240      2250      2260      2270
    •         •         •         •         •         •
CCT TCG CCC TGC CGC ACC AGG TCG CGG CCG TCT CCC GGC GCG AAC GAC
GGC ATC CTG
Pro Ser Pro Cys Arg Thr Arg Ser Arg Pro Ser Pro Gly Ala Asn Asp Gly Ile Leu 2280      2290      2300      2310      2320
       •         •         •         •         •
CGC CTG CAC TCG GCC GAC GTC GAC GCC GAC CCG GTC GAG CTG CGC GTC
GCC GAC CTG
Arg Leu His Ser Ala Asp Val Asp Ala Asp Pro Val Glu Leu Arg Val Ala Asp Leu 2330      2340      2350      2360      2370      2380
  •         •         •         •         •         •
GCC CCC GCG TCG GAC AAG TCC TGG ACG GCG TAC CCC TCG GGC GTC CTG
TGG GCG CTG
Ala Pro Ala Ser Asp Lys Ser Trp Thr Ala Tyr Pro Ser Gly Val Leu Trp Ala Leu

•
 2390      2400      2410      2420      2430      2440
   •         •         •         •         •         •
CGC GAG GCC GGA CAC GAG CTG ACC GGC GCC GAC GTC CAC CTG GCC TCG
ACC GTC CCG
Arg Glu Ala Gly His Glu Leu Thr Gly Ala Asp Val His Leu Ala Ser Thr Val Pro
```

TABLE 1-continued
TRANSLATED SEQUENCE OF *STREPTOMYCES LIVIDANS* GALACTOSE OPERON

```
        2450      2460      2470      2480      2490
         •         •         •         •         •
TCC GGG GCG GGG CTC TCC TCC TCC GCG GCC CTG GAG GTC CGT CCC CTG
GCG ATG AAC
Ser Gly Ala Gly Leu Ser Ser Ser Ala Ala Leu Glu Val Arg Pro Leu Ala Met Asn 2500      2510      2520      2530      2540      2550
   •         •         •         •         •         •
GAC CTG TAC GCC CTC GCG CTG CGC GGC TGG CAG CTG GCC CGG CTG TGC
CAG CGC GCG
Asp Leu Tyr Ala Leu Ala Leu Arg Gly Trp Gln Leu Ala Arg Leu Cys Gln Arg Ala 2560      2570      2580      2590      2600      2610
   •         •         •         •         •         •
GAG AAC GTC TAC GTC GGC GCC CCC GTC GGC ATC ATG GAC CAG ACG GCG
TCC GCC TGC
Glu Asn Val Tyr Val Gly Ala Pro Val Gly Ile Met Asp Gln Thr Ala Ser Ala Cys 2620      2630      2640      2650      2660      2670
         •         •         •         •         •         •
TGC GAG GCG GGC ACG CCC TCT TCC TCG ACA CCC GCG ACC TCT CCC AGC
GGC AGA TCC
Cys Glu Ala Gly Thr Pro Ser Ser Ser Thr Pro Ala Thr Ser Pro Ser Gly Arg Ser 2680      2690      2700      2710      2720
         •         •         •         •         •
CCT TCG ACC TCG CCG CCG AGG GGA TGC GCC TGC TGG TCG TCG ACA CCC
GGG TCA AGC
Pro Ser Thr Ser Pro Pro Arg Gly Cys Ala Cys Trp Ser Ser Thr Pro Gly Ser Ser 2730      2740      2750      2760      2770      2780
 •         •         •         •         •         •
ACT CCC ACA GCG AGG GCG AGT ACC GCA AGC GCC GCG CGG GCT GCG AGA
AGG GCG GCG
Thr Pro Thr Ala Arg Ala Ser Thr Ala Ser Ala Ala Arg Ala Ala Arg Arg Ala Pro 2790      2800      2810      2820      2830      2840
   •         •         •         •         •         •
CGC TGC TGG GCG TCG ACG CGC TGC GAC GTG CCG TAC GCC GAC CTG GAC
GCG GCG CTG
Arg Cys Trp Ala Ser Thr Arg Cys Asp Val Pro Tyr Ala Asp Leu Asp Ala Ala Leu 2850      2860      2870      2880      2890
         •         •         •         •         •
GAG CGG CTG GGC GAC GAG GAG GAG GTG CGC CGC CTG GTC CGG CAC GTG
GTG ACC GAG
Glu Arg Leu Gly Asp Glu Glu Glu Val Arg Arg Leu Val Arg His Val Val Thr Glu 2900      2910      2920      2930      2940      2950
 •         •         •         •         •         •
GAC GAG CGC GTC GAA CGG GTG GTC GCG CTG CTG GAG TCG GCG ACA CCC
GGC GCA TCG
Asp Glu Arg Val Glu Arg Val Val Ala Leu Leu Glu Ser Ala Thr Pro Gly Ala Ser 2960      2970      2980      2990      3000      3010
   •         •         •         •         •         •
GCG CCG TCC TGG TCG AGG GCC ACG CCT GCT GCG CGA CGA CTT CCG CAT
CTC CTG CCC
Ala Pro Ser Trp Ser Arg Ala Thr Pro Ala Ala Arg Arg Leu Pro His Leu Leu Pro 3020      3030      3040      3050      3060
         •         •         •         •         •
CGA GCT GGA CCT GGT CGT CGA CAC GGC CCT GGC CTC CGC GGC CCT CGG
CGC CGG ATG
Arg Ala Gly Pro Gly Arg Arg His Gly Pro Gly Leu Arg Gly Pro Arg Arg Arg Met 3070      3080      3090      3100      3110      3120
 •         •         •         •         •         •
ACC GGC GGC GGC TTC GGC GGC TCG GCG ATC GTC CTG GTG GAG GCC GCC
GCG GTG GAC
Thr Gly Gly Gly Phe Gly Gly Ser Ala Ile Val Leu Val Glu Ala Ala Ala Val Asp
```

TABLE 1-continued
TRANSLATED SEQUENCE OF *STREPTOMYCES LIVIDANS* GALACTOSE OPERON

```
    3130      3140      3150      3160      3170      3180
     •         •         •         •         •         •
GCC GTC ACC AAG GCG GTC GAG GAC GCC TTC GCC GCG GCG GGC CTC AAG
CGT CCG CGG
Ala Val Thr Lys Ala Val Glu Asp Ala Phe Ala Ala Ala Gly Leu Lys Arg Pro Arg 3190      3200      3210      3220      3230      3240
     •         •         •         •         •         •
GTG TTC GAG GCG GTG CCT CGG CGG GGC GCG GCG CCT GGT CTG ACG GTC
AGC CGA GCC
Val Phe Glu Ala Val Pro Arg Arg Gly Ala Ala Pro Gly Leu Thr Val Ser Arg Ala 3250      3260      3270      3280      3290
     •         •         •         •         •
GCT TCA CCA GCG TGT ACT CCG TGA TCC CCG GCG GGT AGT CGG GGA TCA
CGC ACA TGA
Ala Ser Pro Ala Cys Thr Pro ---

3300
 •
GCT GCT AGC CGC
```

EXAMPLE 2

Promoters of the *S. Lividans Gal* Operon a) P1 promoter

(i) Summary

This promoter is galactose inducible, glucose repressible and is the regulatable promoter for the entire *Streptomyces gal* operon. S1 data indicates that the *Streptomyces lividans gal* operon encodes a polycistronic transcript of approximately 3.4 kilobases (Kb). The transcript consists of approximately 1 Kb for galT, followed by approximately 1 Kb each for galE and galK. (See, FIG. 1).

Galactose induction of P1 is mediated, at least in part, by an operator sequence whose 5' end is located 31 bp upstream of the transcription start site and a represssor protein which recognizes the operator.

Figure 2:
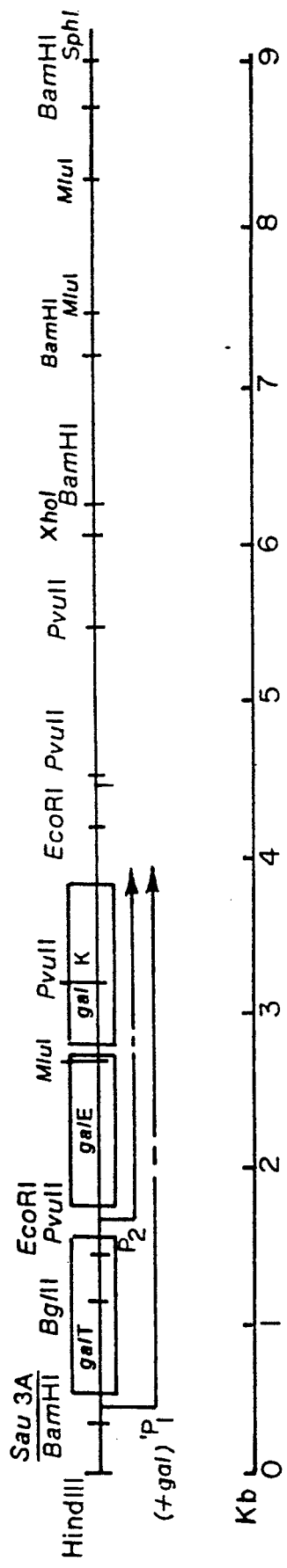
FIG. 2 represents a restriction endonuclease map of plasmid pK21.

(ii) Experimental: Isolation, Localization, and Characterization of the P1 Promoter The sequences upstream of the *Streptomyces lividans galK* ATG were screened for promoters using the *E. coli galK* promoter probe system of Brawner, et al., *Gene*, 40, 191, (1985), in press. The HindIII-MluI fragment (See, Table A, map positions 1-5) was restricted with Sau3AI, ligated into the unique BamHI site of pK21 (FIG. 2), and transformed into *E. coli* K21 (galK) according to the method of Example 1. pK21 is a derivative of pSKO3 and is an *E. coli-Streptomyces* shuttle vector containing the *E. Coli* galK gene (See, FIG. 2. The construction of pSKO3 is described in Rosenberg et al., *Genetic Engineering*, 8, (1986), in press. The clones which expressed galK, i.e., those which had promoter activity, were identified on MacConkey-galactose plates. Two galK+ clones (designated as pK21 MH1 and 2) were transformed into Streptomyces 1326-12 (galK). Extracts from transformants were cultured in Ymglu and Ymgal, and were analyzed by western blot analysis using anti-*E. coli* galactokinase antiserum. The blots showed significantly higher levels of galactokinases in the extracts from the galactose induced cultures.

pK21 MH1 and 2 were shown by restriction analysis to contain a 410 bp Sau3AI insert which is contained within the HindIII and BglII sites (see Table A, map positions 1-2) by Southern blot analysis according to the method of Southern, *J. Mol. Biol.*, 98, 503 (1975). The cloned fragment was analyzed by S1 analysis using RNA isolated from *Streptomyces lividans* 1326-12K and *E. coli* K21 cultures. The fragment yielded a 290 nucleotide protected fragment after S1 digestion (indicating the 5' end of an mRNS 290 bp upstream of the Saw3AI site). Hybridization experiments (using single stranded M13 clones of this region) have identified the direction of transcription as left to right as shown in FIG. 2 (i.e., transcription is going toward galK).

Conventional DNA sequence analysis and additional S1 mapping analysis were used to define the 5' end of the mRNA.

The sequences responsible for regulating galactose induction of P1 were localized by removing sequences upstream of the transcription start site by nuclease Bal31. Any change in promoter function or galactose induction by removal of these sequences was assessed using the *E. coli* galK promoter probe plasmid used to identify P1.

(iii) Construction of Gal Promoter Deletions

Plasmid pHL5 was constructed by cloning a DNA fragment containing 100 bp of sequences downstream from the start of P1 transcription and 216 bp upstream from the start of P1 transcription into plasmid pUC19TT1. Plasmid pUC19TT1 is described in Norrander et al., *Gene*, 26, 101–106 (1983) and has the Unker as pUC18-TT6. See, Example IB. Deletions extending into the upstream sequence preceeding P1 were generated by linearizing pHL5 with HindIII and treating the ends with nuclease Bal31. The uneven ends were subsequently repaired with the Klenow fragment of DNA polymerase I. Bal 31-treated pHL5 was then digested with Bam-HI and run on a 5% acrylamide gal. DNA fragments in the molecular weight range of 100–300 bp were eluted from the gel and subcloned into M13 mp 10 that had been digested with HindII and BamHI. [See, Messing, *Methods in Enzymology*, 101, 20 (1983)]. Individual deletions were then sequenced from the single stranded phage DNA the dideoxy chain termination method of Sanger, et al., cited above.

(iv) Linking the P1 Promoter Deletions to the E. coli galK Gene

The various mp 10 clones were digested with BamHI and HindIII, DNA fragments containing individual deletions were isolated from low-melting point agarose gels and then ligated to pK21 (see, FIG. 2) that had been digested with BamHI and HindIII. After transformation into E. coli MM294, plasmid DNA was isolated for each of the deletion derivatives and transformed into Streptomyces Lividans 12K.

(v) Functional Assessment of Bal 31-Generated Deletions in S. lividans

For each individual promoter deletion, a single thiostrepton resistance transformant was grown to late log in YM base (YEME)+10 ug/ml thiostrepton. Cells were then pelleted, washed once in M56 media and resuspended in M56 media (see Miller, et al., cited above). The washed cells were then used to inoculate YM+01M MOPS (pH 7.2)+10 ug/ml thiostrepton supplemented with 1% galactose or 1% glucose. The cells were grown for 16 hours then assayed for galactokinase activity.

Ten individual pK21 derivatives containing either 120, 67, 55, 34, 31, 24, 20, 18, 10 or 8 bp of sequence upstream of the P1 transcription start site were analyzed for galactokinase expression. These results showed that substantially all the information necessary for galactose induction of P1, (i.e., 10-20 fold greater levels of galactokinase produced in galactose grown cells versus glucose grown cells) is included in the 31 bp of sequence upstream of P1, and that all such information is located in the 67 bp of sequence upstream of P1. A deletion which leaves 34 bp of sequence upstream of P1 is partially inducible by galactose since galactose induced 6-fold greater amounts of galactokinase. Thus, one end of the operator must be situated within the sequences between the −24 and −31 position. The remaining deletions which leave either 20, 18, 10 or 8 bp of upstream sequence result in a constitutive P1 promoter, that is the levels of galactokinase produced were equivalent when cells were grown in the presence of galactose or glucose. Although the promoter deletions which retained 8 and 10 bp of P1 were constitutive, the amount of galactokinase produced was reduced 10 fold in comparison to the promoter deletions which retained 18 to 120 bp of upstream sequence. This result indicates that sequences between the −10 and −18 positions of −1 are essential for promoter fashion.

This data supports a model in which galactose induction of P1 is mediated, at lest in part, by an operator sequence. One end of this sequence is within the region 24 to 31 bp upstream of the P1 transcription start site. Removing part or all of the operator results in a promoter which is partially or totally derepressed. The other end of this sequence has now been defined to be contained within the 16 to 21 bp of sequence upstream of the P1 transcription start site. In addition, we cannot eliminate the possibility that the 3' end of the operator is also within the 100 bp downstream of the transcription start site since these sequences were contained within the smallest region needed to achieve galactose induction. These data also suggest that the factor which interacts with the operator sequence is a repressor protein. Finally, we do not have any evidence which eliminates the possibility that P1 may be controlled by factors other than a repressor (i.e., positive activator such as lambda phage cII protein) to modulate galactose induction promoter transcript.

(vi) Construction of Additional P1 Promoter Mutations

Oligonucleotide directed mutagenesis was performed as originally described by Kunke, et a. 1987 Methods Enzymol. 154:367 using the Mutagene Kit from Biorad (Cat. No. 170-3571) according to the manufacturer's instructions. M13mp18 containing a 196 base pair HindIII-BamHI1 fragment that includes the galP1 promoter from −69 to +103 with respect to the apparent transcription start site was used as template. Fragments containing mutations in a single hexamer were constructed by annealing an oligonucleotide (Sanger et al., 1977 Proc. Natl. Acad. Sci USA 74:5463-5467) containing the desired base changes to wild type gal-P1-containing template DNA. Fragments containing mutations in more than one hexamer were constructed by annealing an oligonucleotide (Sanger et al. 1977 Proc. Natl. Acad. Sci USA 74:5463-5467) containing base changes in one hexamer to a template DNA that contained base changes in the other hexamer. The DNA sequence for each construction was confirmed by subjecting the various promotercontaining fragments to the dideoxy sequencing reactions of Sanger et al. 1977 Proc. Natl. Acad. Sci USA 74:5463-5467 using the Sequenase kit (United States Biochemical Corp., Ohio) and the forward (−40) sequencing primer (P.No. 70736).

(vii) Assay of Promoter Function Using XylE Fusions

To assay the effect of various base changes within the galP1 promoter the 196 bp BamHI-HindIII fragments containing the promoter mutations (prepared as described in Example 2avi, above) were ligated to the larger Bam-HI-HindIII fragment of pXe4 (Ingram, et al., 1989, J. Bacteriol. 171:6617-6624) thereby generating transcriptional fusions between galP1 and a promoterless copy of the xylE gene contained in pXE4. In all cases, plasmid DNA was isolated after transformation to verify the presence of the insert. Plasmid DNA was transformed into S. lividans 1326 using standard procedures (see Hopwood, et al., Genetic Manipulation of Streptomyces-A Laboratory Manual, F. Crows & Sons. Ltd., Norwich, England (1985)). Transformants were selected by overlaying the transformation plates with agar (0.4%) containing 100 mg/ml thiostrepton. Catechol dioxygenase activity was detected on plates and assayed as described by Ingram, 1989, J. Bacteriol., supra, except that the assays were performed at 30 degrees Centigrade. The results are indicated in the following Tables X, Y and Z.

TABLE X

| Catechol dioxygenase activity (% fully induced wild type promoter) | | |
|---|---|---|
| Position/Change | Glucose | Galactose |
| wild type | 7 | 100 |
| −35, G to C | 5 | 206 |
| −34, G to C | 1 | 12 |
| −33, G to C | 7 | 333 |
| −32, G to C | 8 | 9 |

TABLE Y

| Catechol dioxygenase activity (% fully induced wild type promoter) | | |
|---|---|---|
| Position/Change | Glucose | Galactose |
| wild type | 9 | 100 |
| −34, G to A | 34 | 306 |

TABLE Y-continued

| | Catechol dioxygenase activity (% fully induced wild type promoter) | |
|---|---|---|
| Position/Change | Glucose | Galactose |
| −34, G to T | 17 | 850 |
| −32, G to A | 65 | 650 |
| −32, G to T | 8 | 280 |

TABLE Z

| | Catechol dioxygenase activity (% fully induced wild type promoter) | | |
|---|---|---|---|
| Hexamer/Change | Glucose | Galactose | Glycerol |
| wild type | 10 | 100 | 10 |
| (−21 to −16)IV, TCTCAA | 76 | 474 | 75 |
| (−47 to −42)II, TCTCAA | 66 | 1996 | ND |
| (−53 to −48)I, TATCAA | 60 | 75 | 55 |
| (−7 to −2)VI, TATCAA | 37 | 91 | 21 |

ND = not determined b) P2 promoter (i) Summary

The P2 promoter of the *Streptomyces gal* operon is upstream of the galE gene and transcribes both galE and galK genes.

P2 promoter expression is constitutive (i.e., not glucose repressed/galactose inducted) as shown by S1 analysis.

(ii) Experimental: Isolation, Localization, and Characterization of the P2 Promoter The existence of the *Streptomyces gal* operon P2 promoter became apparent when the BglIII-MluI fragment (see, Table A, map positions 2–5) of *S. lividans* 1326 DNA was inserted into plasmid pK21 see, FIG. 2) and galactokinase expression was observed in *Streptomyces lividans* 1326-12K transformed therewith.

DNA sequence analysis and S1 analysis were used to identify the 5' end of the *S. lividans gal* operon P2. The 5' end of the P2 promoter transcript is within the 100 bp upstream of the predicted galE ATG.

EXAMPLE 3

Evidence of a Polycistonic Message in the *Streptomyces Gal* Operon

S1 analysis was used to map the transcripts upstream and downstream of the *Streptomyces lividans gal* operon galK gene. In general, overlapping DNA fragments of 1-2 Kb were isolated from subclones, further restricted, and end labelled. The message was followed from the 3' end of galK to the upstream end at P1.

The 3' end of the *Streptomyces lividans gal* operon transcript probably occurs within the first hundred bases downstream of galK. Fragments 3' labelled at sites within the galK sequence were not protected to their full length (S1 analysis) if they extend into this downstream region. One experiment showed a possible protected region that terminated 50–100 bp downstream of the galK translation stop. The existence of a transcription terminator can be confirmed by conventional techniques by using a terminator probe system. The gal operon transcript clearly does not extend to the PvuII site (see, Table A, map position 8) because no full length protection of 5' labelled PvuII fragments occurs from that site.

5' end labelled fragments from two PvuII fragments, fragment I, (map positions 4–6, See, Table A), and fragment II, (map positions 6–8, see Table A), and the insert of pSau10 were used as sources of probes for S1 walking from the 3' to 5' end of the message. All fragments through this region are protected, except the fragment containing the P2 promoter which shows partial and full protection. The complete protection from S1 digest indicates a polycistronic message which initiates upstream at P1 and continues to approximately 100 bp downstream of galK.

The above data is indirect evidence of a polycistronic mRNA of the *Streptomyces gal* operon. S1 analysis using a long contiguous DNA fragment (e.g., the 4.5 kb HindIII-SacI fragment, see map position 7 of Table A) has been used to confirm the transcript size.

EXAMPLE 4

Localization of *S. Lividans gal* Operon GalE and GalT Genes (i) Summary

The *S. lividans gal* operon galE gene was localized to 1.5 Kb PvuII fragment (mag position, 4–6 of Table A) of pLIVGAL1 (FIG. 1).

The *S. lividans gal* operon galE coding sequences extend through the MluI site (map position 5 of Table A).

The *S. lividans gal* operon galT gene was localized within the 1.15 Kb Nru-PyuIII region (see, Table A, map positions 1a-4) of pSLIVGAL1.

The direction of *S. lividans gal* operon galE and galT transcription is the same as galK gene.

(ii) Experimental

It was necessary to identify the other functions contained on pLIVGAL1; specifically, does this plasmid encode for the enzyme galactose epimerase (galE) or the enzyme galactose transferase (galT). The *Streptomyces gal* operon galK gene was identified by its ability to complement an *E. coli* galK host. Thus, identification of the Streptomyces galT and galE genes was tested for by complemenatation of *E. coli* galE or galT hosts, respectively. An *E. coli* galT− strain (CGSC strain #4467, W3101) and two galE− strains (CGSC strain #4473; W3109 and CGSC strain #4498; PL-2) were obtained to test for complementation by the pSLIVGAL1 clone.

The ca. 9 Kb HindIII-SphI fragment (see, Table A, map positions 1-16) containing the *Streptomyces lividans gal* operon galK gene was inserted into pUC19. This fragment was situated within pUC19 such that transcription from the Plac promoter of pUC19 is in the same direction as the Streptomyces galK gene. pUC19 is described in Yanisch-Perrou, et al., *Gene*, 33, 103 (1983). Complementation was assayed by growth on MacConkey-galactose plates. Cells which can utilize galactose [galE+, galT+, GalK+] will be red to pink on this medium. *E. coli* strain PL-2 (see, Example 2) containing pUC19 with the HindIII-SphI insert were pink on the indicator plate indicating that the HindIII-SphI fragment contains the *Streptomyces lividans* galE gene. The galE gene was later mapped to within the 4.5 Kb Hind-III-SacI (the SacI site is near the region around map position 7-8 of Table A) fragment. If the sequences from the MluI site (map position 5 of Table A) to the SacI site were removed galE complimentation of *E. coli* PL-2 was not detected. The 5' end of the galK gene is 70 base pairs (bp) from the MluI site. Therefore it seemed likely that the MluI site was contained within the 5' or 3' end of the galE gene. To determine the direction of galE transcription, the HindIII-SacI fragment was inserted into pUC18. In this configuration, the *Streptomyces lividans gal* gene is in the opposite orientation with respect to Plac. The pUC18 HindIII-SphI clone did not complement *E. coli* PL-2 indicating the galE is transcribed in the same direction as galK. In addition it was concluded that the MluI site is contained within the 3' end of the galE gene. DNA sequence analysis of the PvuII-MluI fragment (See, Table A, map position 4-5) has identified an open reading frame which encodes for a polypeptide of predicted molecular weight of 33,000 daltons. The 5' end of this reading frame is located approximately 176 bp from the PvuII site (See, Table A, map position 4). Therefore, the sequencing results support the conclusion that the 3' end of galE traverses the MluI site (See, Table A, map position 5).

Similar experiments to localize the galT gene on pSLIVGALI were attempted with the galT hosts.

The region between P1 and the 5' end of galE was sequenced to identify the galT gene. Translation of the DNA sequence to the amino acid sequence identified a reading frame which encodes a protein showing a region of homology to the yeast transferase.

EXAMPLE 5

Galactose Induction of *S. Lividans Gal* Operon GalK Gene (i) Summary

Galactokinase expression is induced within one hour after the addition of galactose to culture medium.

Galactokinase expression is 10 times higher in the presence of galactose versus glucose or no additional carbon source within 6 hours after addition of the sugar.

(ii) Experimental

Galactose induction of the *Streptomyces lividans* galK gene was examined by assaying for galactokinase activity at 1, 3, 6 and 24 hours after the addition of galactose. Two liters of YM+0.1M MOPS (pH 7.2) were inoculated with $2 \times 10^7$ spores of *Streptomyces lividans* 1326. After 21 hours growth, galactose or glucose were added to a final concentration of 1%. One, three, six and twenty four hours after the addition of sugar, cells were isolated and assayed for galactokinase activity. Total RNA was prepared by procedures described in Hopwood et al., cited above.

An increase in galactokinase synthesis was observed one hour after the addition of galactose. The increase continued over time (1 to 24 hours). S1 analysis or RNA isolated from the induced cultures confirmed that the increase in GalK activity was due to increased levels of the P1 promoter transcript.

The S1 data and the induction studies suggest the following model for gene expression with the *Streptomyces gal* operon. The P1 promoter is the galactose inducible promoter. The P1 transcript includes galT, galE and galK. The P2 promoter is constitutive and its transcript includes galE and galK.

It is interesting to note that the *E. coli gal* operon also has two promoters, P1, P2. [See, Nusso et al., *Cell*, 12, 847 (1977)]. P1 is activated by cAMP-CRP binding whereas P2 is inhibited by cAMP-CRP. Translation of the *E. coli gal* operon galE coding sequence is more efficient when transcription initiates at P2 which serves to supply a constant source of epimerase even in the absence of galactose or the presence of glucose [See, Queen et al., *Cell*, 25, 251 (1981)]. The epimerase functions to convert galactose to glucose 1-phosphate during galactose utilization and convert UDP-glucose to UDP-galactose which is required for *E. coli* cell wall biosynthesis. It is possible that the P2 promoter of the Streptomyces galE operon also serves to supply epimerase and galactokinase in the absence of galactose or during secondary metabolism.

EXAMPLE 6

The *S. Coelicolor Gal* Operon (i) Summary

The restriction map of a fragment containing the *S. coelicolor galK* gene is identical to the restriction map of the *S. lividans gal* operon. (See, FIG. 3).

*S. coelicolor* can grow on minimal media containing galactose as the sole carbon source.

Galactokinase expression in *S. coelicolor* is induced by the addition of galactose to the growth media.

A promoter analogous and most likely identical to P1 is responsible for galactose induction of the *S. coelicolor gal* operon.

(ii) Experimental

Figure 3:
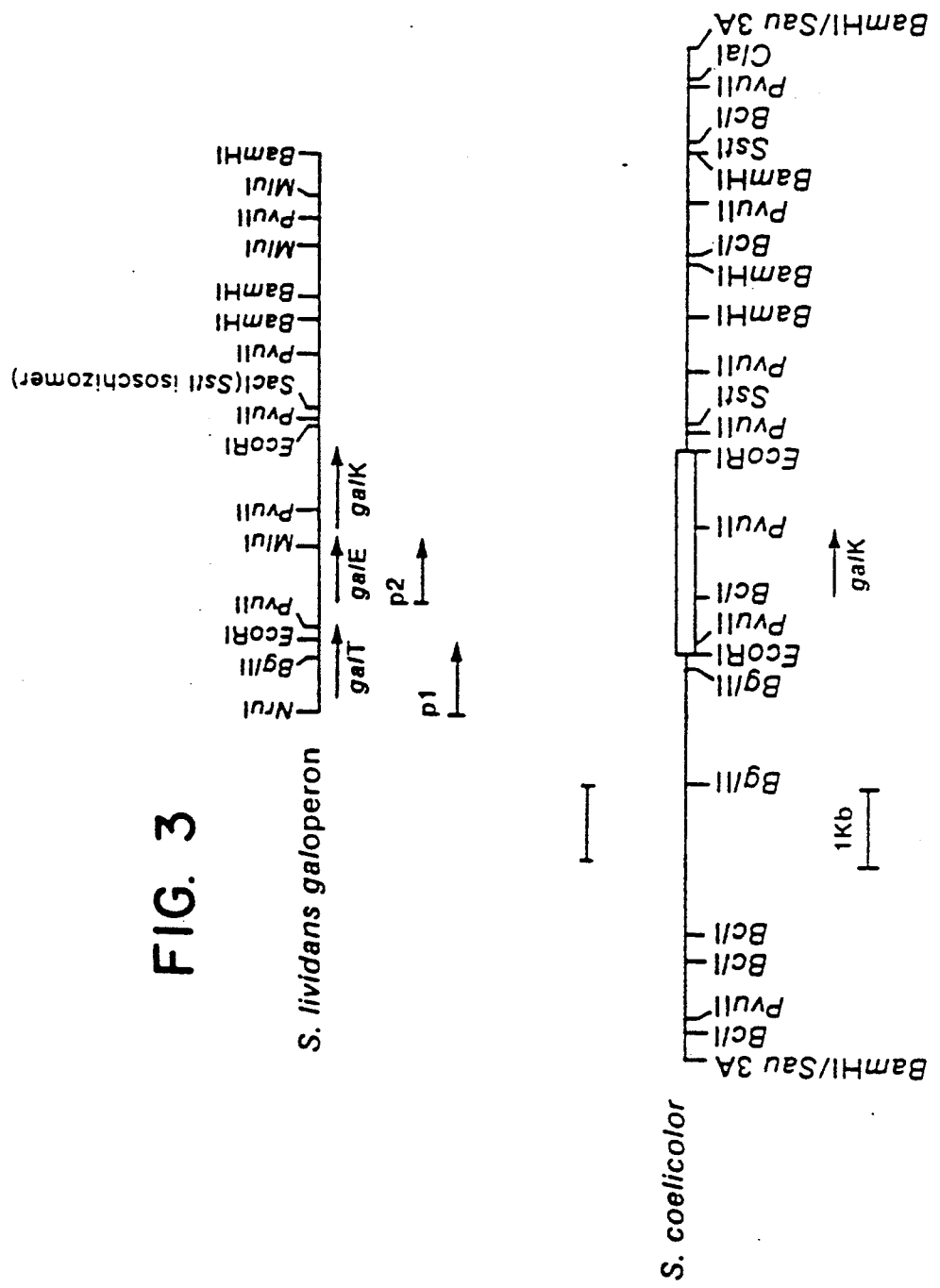
FIG. 3 represents a comparison of the restriction endonuclease maps of the *S. lividans* gal operon and a restriction fragment containing the *S. coelicolor* galK gene.

An approximately 14 kb partial Sau3A fragment containing the *S. coelicolor galK* gene was isolated by K. Kendall and J. Cullum at the University of Manchester Institute of Science and Technology, Manchester, UK (unpublished data; personal communication). They were able to localize the *S. coelicolor galK* gene within a 3 kb EcoRI fragment by complimentation of a *S. coelicolor galK* mutant. The position of the number of restriction sites within the *S. lividans gal* operon are identical to those found within, upstream and downstream of the EcoRI fragment containing the *S. coelicolor galK* gene (FIG. 3). Thus, it seems likely that the gene organization of the *S. lividans gal* operon is identical to the *S. lividans gal* operon.

Galactose induction of the *S. coelicolor galK* gene was examined by immunoblotting. *S. coelicolor* was grown in YM+1% galactose or 1% glucose (Ymglu or Ymgal) for 20 hours at 28° C. Galactokinase expression was detected using rabbit antisera prepared against purified *E. coli* galactokinase. The protein detected was the approximate size of the *E. coli* and *S. lividans galK* gene product. Galactokinase expression is galactose induced since it was detected only when *S. coelicolor* was grown in Ym+galactose (Ymgal).

S1 nuclease protection studies were performed to determine if galactose induction of the *S. coelicolor gal* operon is directed by a promoter analogous to the *S. lividan* P1 promoter. RNA was isolated from *S. coelicolor* grown in Ym+1% galactose or 1% glucose (Ymgal or Ymglu). The hybridization probe used for S1 analysis of the RNA was 410 pb Sau3A fragment which contains the *S. lividans* P1 promoter. Its transcription start site and the 5' end of the galT gene. The S1 protected fragment detected by this analysis co-migrated with the protected fragment detected when the probe was hybridized to RNA isolated from *S. lividans* grown in the presence of galactose. Thus, this result shows that galactose induction of the *S. coelicolor gal* operon is directed by a sequence indistinguishable from the *S. lividans* P1 promoter.

It should be noted that the following strains of Streptomyces have been observed to be able to grow on medium containing galactose as the only carbon source;

*S. albus* J1074 (obtained from Dr. Chater, John Innes Foundation, Norwich, England)
*S. carzinostaticus*—ATCC accession number 15944
*S. carzinostaticus*—ATTC accession number 15945
*S. antifibrinolyticus*—ATCC accession number 21869
*S. antifibrinolyticus*—ATCC accession number 21870
*S. antifibrinolyticus*—ATCC accession number 21871
*S. longisporus*—ATCC accession number 23931

The abbreviation "ATCC" stands for the American Type Culture Collection, Rockville, Md., U.S.A.

While the above descriptions and Examples fully describe the invention and the preferred embodiments thereof, it is understood that the invention is not limited to the particular disclosed embodiments. Thus, the invention includes all embodiments coming within the scope of the following claims.

What is claimed is:

1. A recombinant DNA molecule comprising a *Streptomyces lividans* gal operon containing a wild-type gal operon P1 promoter or a regulatable and function P1 deletion derivative.

2. The molecule of claim 1 which has the following coding sequence:

```
        -120           -110           -100           -90            -80            -70
         •              •              •              •              •              •
CTA CGC CTC CGC GTT CAG TAA TTG AAC ACT TTT GGT GAT GAA CTT TGT TTG ATT GTG

-60            -50            -40            -30            -20
          •              •              •              •              •
ATG TGA CAG GGG GGT GGT GGG TTG TGA TGT GTT ATG TTT GAT TGT GTT GGA TGA TTG
                                                                              galP1

-10             1              10             20             30             40
          •              •              •              •              •              •
ACG GGC GTC CTG GTG ACT CAT GGG TGG GTG CAG AGG AGT GCG GCA GTG AAG AAG ACC
                     Met Thr His Gly Trp Val Gln Arg Ser Ala Ala Val Lys Lys Thr
                     galT 50             60             70             80             90             100
          •              •              •              •              •              •
TCG ACC CGG CTG GCC GAC GGC CGT GAG CTG GTC TAC TAC GAC CTG CGC GAC GAC ACC
Ser Thr Arg Leu Ala Asp Gly Arg Glu Leu Val Tyr Tyr Asp Leu Arg Asp Asp Thr 110            120            130            140            150
                 •              •              •              •              •
GTG CGC GAC GCC GTG GAC CGC CGT CCG CTG GAG CGG ACC GTC ACC ACG TCC GAG GTG
Val Arg Asp Ala Val Asp Arg Arg Pro Leu Glu Arg Thr Val Thr Thr Ser Glu Val 160            170            180            190            200            210
   •              •              •              •              •              •
CGA CGC GAC CCG CTG CTC GGC GAC TCC GCG CCG TCG CGC CTC GCA CCG GCA GGG GCG
Arg Arg Asp Pro Leu Leu Gly Asp Ser Ala Pro Ser Arg Leu Ala Pro Ala Gly Ala 220            230            240            250            260            270
   •              •              •              •              •              •
CAC CTA CCA TCC GCC GGC CGA CCA GTG CCC GCT GTG CCc GTC GGA CGG GGA ACG GCT
His Leu Pro Ser Ala Gly Arg Pro Val Pro Ala Val Pro Val Gly Arg Gly Thr Ala 280              290            300            310            320            330
          •                •              •              •              •              •
GAG CGA GAT CCG GCC TAT GAC GTG GTG GTC TTC GAG AAT CGC TTT CCC TCG CTG GCC
Glu Arg Asp Pro Ala Tyr Asp Val Val Val Phe Glu Asn Arg Phe Pro Ser Leu Ala 340            350            360            370            380
                 •              •              •              •              •
GGT GAC TCC GGG CGC TGC GAG GTC GTC TGC TTC ACC TCC GAC CAC GAC GCC TCC TTC
Gly Asp Ser Gly Arg Cys Glu Val Val Cys Phe Thr Ser Asp His Asp Ala Ser Phe 390            400            410            420            430            440
   •              •              •              •              •              •
GCC GAC CTG AGC GAG GAG CAG GCC CGG CTG GTC GTC GAC GCC TGG ACG GAC CGC ACC
Ala Asp Leu Ser Glu Glu Gln Ala Arg Leu Val Val Asp Ala Trp Thr Asp Arg Thr 450            460            470            480            490            500
          •              •              •              •              •              •
TCC GAG CTG TCC CAT CTG CCC TCC GTT GAA CAG GTG TTC TGC TTC GAG AAC CGG GGC
Ser Glu Leu Ser His Leu Pro Ser Val Glu Gln Val Phe Cys Phe Glu Asp Arg Gly 510            520            530            540            550
                 •              •              •              •              •
GCC GAG ATC GGG GTG ACG CTG GGT CAC CCG CAC GGG CAG ATC TAC GCC TAC CCG TTC
Ala Glu Ile Gly Val Thr Leu Gly His Pro His Gly Gln Ile Tyr Ala Tyr Pro Phe 560            570            580            590            600            610
   •              •              •              •              •              •
ACC ACC CCC CGC ACC GCC CTG ATG CTC CGT TCA CTC GCC GCC CAC AAG GAC GCG ACG
Thr Thr Pro Arg Thr Ala Leu Met Leu Arg Ser Leu Ala Ala His Lys Asp Ala Thr 620            630            640            650            660            670
          •              •              •              •              •              •
GGC GGG GGG AAC CTG TTC GAC TCC GTG CTG GAG GAG GAG CTG GCC GGT GAG CGG GTC
Gly Gly Gly Asn Leu Phe Asp Ser Val Leu Glu Glu Glu Leu Ala Gly Glu Arg Val
```

```
              680          690          700          710          720
                *            *            *            *            *
GTC CTG GAG GGT GAG CAC TGG GCC GCC TTC GTC GCG TAC GGC GCG CAC TGG CCG TAC
Val Leu Glu Gly Glu His Trp Ala Ala Phe Val Ala Tyr Gly Ala His Trp Pro Tyr 730          740          750          760          770          780
      *            *            *            *            *            *
 GAG GTG CAC CTC TAC CCG AAG CGG CGG GTG CCC GAT CTG CTC GGG CTC GAC GAG GCG
 Glu Val His Leu Tyr Pro Lys Arg Arg Val Pro Asp Leu Leu Gly Leu Asp Glu Ala 790          800          810          820          830          840
      *            *            *            *            *            *
GCT CGC ACA GAA TTC CCC AAG GTC TAC CTG GAG CTG CTG AGG CGT TTC GAC CGG ATC
Ala Arg Thr Glu Phe Pro Lys Val Tyr Leu Glu Leu Leu Arg Arg Phe Asp Arg Ile 850          860          870          880          890          900
      *            *            *            *            *            *
TTC GGC GAG GGC GAG CCC CCG ACC CCC TAC ATC GCG GCC TGG CAC CAG GCG CCG TTC
Phe Gly Glu Gly Glu Pro Pro Thr Pro Tyr Ile Ala Ala Trp His Gln Ala Pro Phe 910          920          930          940          950
           *            *            *            *            *
GGG CAG CTG GAG TTC GAG GGT GTG ACG CGC GAC GAC TTC GCG CTC CAC CTG GAA CTT
Gly Gln Leu Glu Phe Glu Gly Val Thr Arg Asp Asp Phe Ala Leu His Leu Glu Leu 960          970          980          990         1000         1010
      *            *            *            *            *            *
TTC ACT TCC GCC GTA CGT CCG GCA AGC TGA AGT TCC TCG CGG GCT CCG AAT CCG GCA
Phe Thr Ser Ala Val Arg Pro Ala Ser ---              galP2

1020         1030         1040         1050         1060         1070
           *            *            *            *            *            *
TGAACG TGTTCATCAA CGACGTACCC CCGGAGCGCG CGGCCGAGCG ACTGCGAGAG GTAGCGAG 1080         1090         1100         1110         1120         1130
     *            *            *            *            *            *
TTC ATG AGC GGG AAG TAC CTG GTG ACA GGT GGT GCC GGA TAC GTC GGC AGC GTC GTC
    Met Ser Gly Lys Tyr Leu Val Thr Gly Gly Ala Gly Tyr Val Gly Ser Val Val
    galE 1140         1150         1160         1170         1180         1190
     *            *            *            *            *            *
GCC CAG CAC TTG GTG GAG GCG GGG AAC GAG GTC GTG GTG CTG CAC AAT CTG TCG ACC
Ala Gln His Leu Val Glu Ala Gly Asn Glu Val Val Val Leu His Asn Leu Ser Thr 1200         1210         1220         1230         1240
           *            *            *            *            *
GGC TTC CGT GAG GTG TGC CGG CGG GTG CCT CGT TCG TCG AGG CGA CAT CCG GGA CGC
Gly Phe Arg Glu Val Cys Arg Arg Val Pro Arg Ser Ser Arg Arg His Pro Gly Arg 1250         1260         1270         1280         1290         1300
     *            *            *            *            *            *
 CGC CAA GTG CGT GGA CGG CTC TCG TTC GAC GGC GTG CTG CAC TTC GCC GCC TTC TCC
 Arg Gln Val Arg Gly Arg Leu Ser Phe Asp Gly Val Leu His Phe Ala Ala Phe Ser 1310         1320         1330         1340         1350         1360
     *            *            *            *            *            *
CAG GTC GGC GAG TCG GTC GTG AAG CCC GAG AAG TAC TGG GAC AAC AAC GTC GGT GGC
Gln Val Gly Glu Ser Val Val Lys Pro Glu Lys Tyr Trp Asp Asn Asn Val Gly Gly 1370         1380         1390         1400         1410         1420
      *            *            *            *            *            *
ACC ATG GCG CTG CTG GAG GCC ATG CGG GGC GCG GGT GTG CGG CGG CTC GTC TTC TCC
Thr Met Ala Leu Leu Glu Ala Met Arg Gly Ala Gly Val Arg Arg Leu Val Phe Ser 1430         1440         1450         1460         1470
            *            *            *            *            *
TCC ACG GCC GCC ACG TAC GGC GAG CCC GAG CAG GTT CCC ATC GTC GAG TCC GCG CCG
Ser Thr Ala Ala Thr Tyr Gly Glu Pro Glu Gln Val Pro Ile Val Glu Ser Ala Pro 1480         1490         1500         1510         1520         1530
     *            *            *            *            *            *
ACG AGG CCC ACC AAT CCG TAC GGC GCC TCG AAG CTC GCC GTC GAC CAC ATG ATC ACC
Thr Arg Pro Thr Asn Pro Tyr Gly Ala Ser Lys Leu Ala Val Asp His Met Ile Thr 1540         1550         1560         1570         1580         1590
     *            *            *            *            *            *
GGC GAG GCG GCG GCC CAC GGG CTG GGC GCG GTC TCC GTG CCG TAC TTC AAC GTC GCG
Gly Glu Ala Ala Ala His Gly Leu Gly Ala Val Ser Val Pro Tyr Phe Asn Val Ala
```

```
                 1600          1610          1620          1630          1640
GGC GCG TAC GGG GAG TAC GGC GAG CGC CAC GAC CCC GAG TCG CAT CTG ATT CCG CTG
Gly Ala Tyr Gly Glu Tyr Gly Glu Arg His Asp Pro Glu Ser His Leu Ile Pro Leu 1650          1660          1670          1680          1690          1700
GTC CTT CAA GTG GCG CAG GGC AGG CGG GAG GCC ATC TCC GTC TAC GGC GAC GAC TAC
Val Leu Gln Val Ala Gln Gly Arg Arg Glu Ala Ile Ser Val Tyr Gly Asp Asp Tyr 1710          1720          1730          1740          1750          1760
CCG ACG CCG GAC CGA CCT GTG TGC GCG ACT ACA TCC ACG TCG CCG ACC TGG CCG AGG
Pro Thr Pro Asp Arg Pro Val Cys Ala Thr Thr Ser Thr Ser Pro Thr Trp Pro Arg 1770          1780          1790          1800          1810
CCC ACC TGC TGG CCG TGC GCC GCC GCC CCG GGC GAG CAC CTC ATC TGC AAC CTG GGC
Pro Thr Cys Trp Pro Cys Ala Ala Ala Pro Gly Glu His Leu Ile Cys Asn Leu Gly 1820          1830          1840          1850          1860          1870
AAC GGC AAC GGC TTC TCC GTC CGC GAG GTC GTC GAG ACC GTG CGG CGG GTG ACG GGC
Asn Gly Asn Gly Phe Ser Val Arg Glu Val Val Glu Thr Val Arg Arg Val Thr Gly 1880          1890          1900          1910          1920          1930
CAT CCG ATC CCC GAG ATC ATG GCC CCG CGC CGC GGG CGC GAC CCG GCG GTC CTG GTC
His Pro Ile Pro Glu Ile Met Ala Pro Arg Arg Gly Arg Asp Pro Ala Val Leu Val 1940          1950          1960          1970          1980          1990
GCG TCG GCC GGC ACC GCC CGC GAG AAG CTG GGC TGG AAC CCG TCC CGC GCG GAC CTC
Ala Ser Ala Gly Thr Ala Arg Glu Lys Leu Gly Trp Asn Pro Ser Arg Ala Asp Leu 2000          2010          2020          2030          2040
GCC ATC GTG TCG GAC GCG TGG GAG TTG CCG CAG CGG CGC GCG GGC CAG TAG TA
Ala Ile Val Ser Asp Ala Trp Glu Leu Pro Gln Arg Arg Ala Gly Gln —

2050          2060          2070          2080          2090          2100
ACC GCA GTT ACC GGA AAG GCG AGG GGT CAG GGC ATG GGC GAG GCT GTC GGG AAC CCG
                                             Met Gly Glu Ala Val Gly Glu Pro
                                             galK 2110          2120          2130          2140          2150
TCG GCG AGC GGT TCC GGG AGC TGT ACG GGG CGG AGC CGG AGG GGG TGT GGG CGC CGA
Ser Ala Ser Gly Ser Gly Ser Cys Thr Gly Arg Ser Arg Arg Gly Cys Gly Arg Arg 2160          2170          2180          2190          2200          2210
GCG GGC CGG GAG AAC CTC ATC GGG GAG CAC ACC GAC TAC AAC GAC GGC TTC GTC ATG
Ala Gly Arg Glu Asn Leu Ile Gly Glu His Thr Asp Tyr Asn Asp Gly Phe Val Met 2220          2230          2240          2250          2260          2270
CCT TCC CCC TGC CGC ACC AGG TCG CGG CCG TCT CCC GGC GCG AAC GAC GGC ATC CTG
Pro Ser Pro Cys Arg Thr Arg Ser Arg Pro Ser Pro Gly Ala Asn Asp Gly Ile Leu 2280          2290          2300          2310          2320
CGC CTG CAC TCG GCC GAC GTC GAC GCC GAC CCG GTC GAG CTG CGC GTC GCC GAC CTG
Arg Leu His Ser Ala Asp Val Asp Ala Asp Pro Val Glu Leu Arg Val Ala Asp Leu 2330          2340          2350          2360          2370          2380
GCC CCC GCG TCG GAC AAG TCC TGG ACG GCG TAC CCC TCG GGC GTC CTG TGG GCG CTG
Ala Pro Ala Ser Asp Lys Ser Trp Thr Ala Tyr Pro Ser Gly Val Leu Trp Ala Leu 2390          2400          2410          2420          2430          2440
CGC GAG GCC GGA CAC GAG CTG ACC GGC GCC GAC GTC CAC CTG GCC TCG ACC GTC CCG
Arg Glu Ala Gly His Glu Leu Thr Gly Ala Asp Val His Leu Ala Ser Thr Val Pro 2450          2460          2470          2480          2490
TCC GGG GCG GGG CTC TCC TCC TCC GCG GCC CTG GAG GTC CGT CCC CTG GCG ATG AAC
Ser Gly Ala Gly Leu Ser Ser Ser Ala Ala Leu Glu Val Arg Pro Leu Ala Met Asn
```

-continued

```
     2500         2510         2520         2530         2540         2550
GAC CTG TAC GCC CTC GCG CTG CGC GGC TGG CAG CTG GCC CGG CTG TGC CAG CGC GCG
Asp Leu Tyr Ala Leu Ala Leu Arg Gly Trp Gln Leu Ala Arg Leu Cys Gln Arg Ala 2560         2570         2580         2590         2600         2610
GAG AAC GTC TAC GTC GGC GCC CCC GTC GGC ATC ATG GAC CAG ACG GCG TCC GCC TGC
Glu Asn Val Tyr Val Gly Ala Pro Val Gly Ile Met Asp Gln Thr Ala Ser Ala Cys 2620         2630         2640         2650         2660         2670
TGC GAG GCG GGC ACG CCC TCT TCC TCG ACA CCC GCG ACC TCT CCC AGC GGC AGA TCC
Cys Glu Ala Gly Thr Pro Ser Ser Ser Thr Pro Ala Thr Ser Pro Ser Gly Arg Ser 2680         2690         2700         2710         2720
CCT TCG ACC TCG CCG CCG AGG GGA TGC GCC TGC TGG TCG TCG ACA CCC GGG TCA AGC
Pro Ser Thr Ser Pro Pro Arg Gly Cys Ala Cys Trp Ser Ser Thr Pro Gly Ser Ser 2730         2740         2750         2760         2770         2780
ACT CCC ACA GCG AGG GGG AGT ACG GCA AGC GCC GCG CGG GCT GCG AGA AGG GCG CCG
Thr Pro Thr Ala Arg Ala Ser Thr Ala Ser Ala Ala Arg Ala Ala Arg Arg Ala Pro 2790         2800         2810         2820         2830         2840
CGC TGC TGG GCG TCG ACG CGC TGC GAC GTG CCG TAC GCC GAC CTG GAC GCG GCG CTG
Arg Cys Trp Ala Ser Thr Arg Cys Asp Val Pro Tyr Ala Asp Leu Asp Ala Ala Leu 2850         2860         2870         2880         2890
GAG CGG CTG GGC GAC GAG GAG GAG GTG CGC CGC CTG GTC CGG CAC GTG GTG ACC GAG
Glu Arg Leu Gly Asp Glu Glu Glu Val Arg Arg Leu Val Arg His Val Val Thr Glu 2900         2910         2920         2930         2940         2950
GAC GAG CGC GTC GAA CGG GTG GTC GCG CTG CTG GAG TCG GCG ACA CCC GGC GCA TCG
Asp Glu Arg Val Glu Arg Val Val Ala Leu Leu Glu Ser Ala Thr Pro Gly Ala Ser 2960         2970         2980         2990         3000         3010
GCG CCG TCC TGG TCG AGG GCC ACG CCT GCT GCG CGA CGA CTT CCG CAT CTC CTG CCC
Ala Pro Ser Trp Ser Arg Ala Thr Pro Ala Ala Arg Arg Leu Pro His Leu Leu Pro 3020         3030         3040         3050         3060
CGA GCT GGA CCT GGT CGT CGA CAC GGC CCT GGC CTC CGC GGC CCT CGG CGC CGG ATG
Arg Ala Gly Pro Gly Arg Arg His Gly Pro Gly Leu Arg Gly Pro Arg Arg Arg Met 3070         3080         3090         3100         3110         3120
ACC GGC GGC GGC TTC GGC GGC TCG GCG ATC GTC CTG GTG GAG GCC GCC GCG GTG GAC
Thr Gly Gly Gly Phe Gly Gly Ser Ala Ile Val Leu Val Glu Ala Ala Ala Val Asp 3130         3140         3150         3160         3170         3180
GCC GTC ACC AAG GCG GTC GAG GAC GCC TTC GCC GCG GCG GGC CTC AAG CGT CCG CGG
Ala Val Thr Lys Ala Val Glu Asp Ala Phe Ala Ala Ala Gly Leu Lys Arg Pro Arg 3190         3200         3210         3220         3230         3240
GTG TTC GAG GCG GTG CCT CGG CGG GGC GCG GCG CCT GGT CTG ACG GTC AGC CGA GCC
Val Phe Glu Ala Val Pro Arg Arg Gly Ala Ala Pro Gly Leu Thr Val Ser Arg Ala 3250         3260         3270         3280         3290
GCT TCA CCA GCG TGT ACT CCG TGA TCC CCG GCG GGT AGT CGG GGA TCA CGC ACA TGA
Ala Ser Pro Ala Cys Thr Pro ---

3300
GCT GCT AGC CGC
```

3. The molecule of claim 1 which further comprises a foreign functional DNA sequence operatively linked to such operon.

4. A recombinant DNA vector comprising the molecule of claim 3, and, optionally, additionally comprising a replicon.

5. A transformed host microorganism comprising the molecule of claim 3.

6. A transformed host microorganism comprising the recombinant DNA vector of claim 4.

7. A method of regulating the expression of a foreign functional DNA sequence which comprises cultivating a transformed host microorganism which contains the recombinant DNA vector of claim 4 under appropriate conditions such that expression of the sequence is regulatable.

8. A recombinant DNA molecule comprising a *Streptomyces lividans gal* operon P2 promoter expression unit.

9. The molecule of claim 8 which is a *S. lividans gal* operon P2 promoter expression unit.

10. The molecule of claim 8 which further comprises a foreign functional DNA sequence operatively linked to such expression unit.

11. A recombinant DNA vector comprising the molecule of claim 10 and, optionally, additionally comprising a replicon.

12. A transformed host microorganism comprising a recombinant DNA molecule wherein such molecule comprises the molecule of claim 10.

13. A transformed host microorganism comprising the recombinant DNA vector of claim 11.

14. A recombinant DNA molecule comprising a *Streptomyces lividans gal* operon P1 promoter regulated region or any regulatable and functional deletion derivative thereof.

15. The molecule of claim 14 wherein the region is a *S. lividans gal* operon P1 promoter regulated region.

16. The molecule of claim 14 which further comprises a foreign functional DNA sequence operatively linked to such regulated region.

17. A recombinant DNA vector comprising the molecule of claim 16, and, optionally, additionally comprising a replicon.

18. A transformed host microorganism comprising the molecule of claim 16.

19. A transformed host microorganism comprising a recombinant DNA vector of claim 14.

20. A method of regulating the expression of a foreign functional DNA sequence which comprises cultivating a transformed host microorganism which contains the recombinant DNA vector of claim 17 under appropriate conditions such that expression of the sequence is regulatable.

21. A recombinant DNA molecule comprising a *Streptomyces lividans gal* operon P2 promoter.

22. The molecule of claim 21 which further comprises a foreign functional DNA sequence operatively linked to the P2 promoter.

23. A recombinant DNA vector comprising the molecule of claim 22 and, optionally, additionally comprising a replicon.

24. A transformed host microorganism comprising the molecule of claim 22.

25. A transformed host microorganism comprising the recombinant DNA vector of claim 23.

26. A recombinant DNA molecule comprising a *Streptomyces lividans gal* operon P1 promoter or any regulatable and functional deletion derivative thereof.

27. The molecule of claim 26 wherein the promoter is a *S. lividans gal* operon P1 promoter.

28. The molecule of claim 26 which further comprises a foreign functional DNA sequence operatively linked to the P1 promoter.

29. A recombinant DNA vector comprising the molecule of claim 28, and, optionally, additionally comprising a replicon.

30. A transformed host microorganism comprising the molecule of claim 28.

31. A transformed host microorganism comprising the recombinant DNA vector of claim 29.

32. A method of regulating the expression of a foreign functional DNA sequence which comprises cultivating a transformed host microorganism which contains the recombinant DNA vector of claim 29 under appropriate conditions such that expression of the sequence is regulatable.

33. A recombinant DNA molecule comprising a *Streptomyces lividans gal* operon galE gene.

34. The molecule of claim 33 which further comprises a foreign functional DNA sequence operatively linked to the galE gene.

35. A transformed host microorganism comprising the molecule of claim 34.

36. A recombinant DNA molecule comprising a *Streptomyces lividans gal* operon galT gene.

37. The molecule of claim 36 which further comprises a foreign function DNA sequence operatively linked to the galT gene.

38. A transformed host microorganism comprising the molecule of claim 37.

39. A recombinant DNA molecule comprising a *Streptomyces lividans gal* operon galK gene.

40. The molecule of claim 39 which further comprises a foreign functional DNA sequence operatively linked to the galK gene.

41. A transformed host microorganism comprising the molecule of claim 40.

42. A method of enabling a nongalactose utilizing host bacterial cell to utilize galactose which comprises transforming such host with a recombinant DNA vector or molecule comprising a *Streptomyces lividans gal* operon, or any portion of the *Streptomyces lividans gal* operon which is adequate to enable such transformed host to utilize galactose.

43. A transformed host prepared by the method of claim 42.

* * * * *

UNITED STATES PATENT AND TRADEMARK OFFICE
CERTIFICATE OF CORRECTION

PATENT NO. : 5,242,809
DATED : September 7, 1993
INVENTOR(S) : Adams, Brawner, Fornwald and Schmidt It is certified that error appears in the above-indentified patent and that said Letters Patent is hereby corrected as shown below:

Column 36,
At claim 1, line 3, delete "function" and substitute --functional--; and after "P1", insert --promoter--.
Column 39 and 41,
At claim 2, in the coding sequence, at position 2220, delete "C" and substitute --G--; and at position 2744, delete "G" and substitute --C--.

Signed and Sealed this

Twenty-sixth Day of July, 1994

*Attest:*

BRUCE LEHMAN

*Attesting Officer*  *Commissioner of Patents and Trademarks*